(12) United States Patent
Tada

(10) Patent No.: US 8,043,074 B2
(45) Date of Patent: Oct. 25, 2011

(54) BLOOD PUMP DEVICE

(75) Inventor: Saho Tada, Tokyo (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 1160 days.

(21) Appl. No.: 11/812,727

(22) Filed: Jun. 21, 2007

(65) Prior Publication Data

US 2007/0297923 A1    Dec. 27, 2007

(30) Foreign Application Priority Data

Jun. 23, 2006  (JP) .................................. 2006-173928

(51) Int. Cl.
*F04B 35/04* (2006.01)

(52) U.S. Cl. .................. 417/423.12; 415/123; 415/126; 415/133

(58) Field of Classification Search ............. 417/423.12; 415/123, 126, 128–129, 131–133, 204, 206
See application file for complete search history.

(56) References Cited

U.S. PATENT DOCUMENTS

| | | | |
|---|---|---|---|
| 4,416,582 A * | 11/1983 | Glass | 415/59.1 |
| 6,368,075 B1 | 4/2002 | Fremercy | |
| 6,581,476 B1 | 6/2003 | Fremercy | |
| 6,742,999 B1 | 6/2004 | Nüsser et al. | |
| 6,840,735 B2 * | 1/2005 | Yaegashi et al. | 415/42 |
| 7,033,147 B2 | 4/2006 | Yanai et al. | |
| 2005/0287022 A1 | 12/2005 | Yaegashi et al. | |

FOREIGN PATENT DOCUMENTS

| | | |
|---|---|---|
| JP | 2002-303288 A | 10/2002 |
| JP | 2003-201992 A | 7/2003 |
| JP | 2003-210572 A | 7/2003 |
| JP | 2005-270345 A | 10/2005 |
| JP | 2005-287598 A | 10/2005 |

* cited by examiner

*Primary Examiner* — Charles Freay
*Assistant Examiner* — Patrick Hamo
(74) *Attorney, Agent, or Firm* — Buchanan Ingersoll & Rooney PC

(57) ABSTRACT

A blood pump device comprises a housing having a blood inflow port and a blood outflow port, an impeller having a magnetic body or bodies and rotated in a non-contact state in relation to the inside surface of the housing to feed blood, an impeller rotating torque generating section for attracting the impeller from the outside of the housing and rotating the impeller, and a non-contact type bearing mechanism enabling the rotation in the non-contact state of the impeller inside the housing. An impeller fixing member is detachably mounted to the housing and prevents the impeller from moving inside the housing, whereby the impeller can be prevented from moving inside the housing before use, and damage to the impeller or the housing inside surface can be avoided.

18 Claims, 17 Drawing Sheets

BLOOD PUMP DEVICE

TECHNICAL FIELD

The present invention generally relates to a blood pump device for feeding blood.

BACKGROUND DISCUSSION

Blood pumps include intracorporeal embedded type pumps, so-called artificial hearts, and pumps for extracorporeal use. One requirement associated with both types of blood pumps is that they not generate hemolyzation or thrombus. In addition, the former type of blood pump is required to meet especially high technical demands because they are difficult to replace.

In recent years, attention has been directed at developing a continuous flow pump, for use as a blood pump, that is capable of being easily reduced in size. In the continuous flow type pumps, a magnetic bearing or hydrodynamic bearing, in which an impeller and a blood chamber do not make contact in the pump, is often used in order to restrain the generation of hemolyzation or thrombus.

In the case of both the magnetic bearing and the hydrodynamic bearing, the impeller for feeding blood is levitated in the blood chamber, by use of an attractive force (or repulsive force) of a permanent magnet and a force balancing therewith. The attractive force (or repulsive force) of an electromagnet is used as the balancing force in the case of the magnetic bearing, and a force generated by hydrodynamic grooves is used as the balancing force in the case of the hydrodynamic bearing.

A magnetic bearing pump has been proposed in Japanese Patent Laid-open No. 2002-303288. This centrifugal type liquid pump device 1 includes: a pump section 2 having an impeller 21 rotated inside a housing 20; an impeller rotating torque generating section 3 including a rotor 31 having magnets 33 for attracting the impeller 21, and a motor 34 for rotating the rotor 31; a pump device body section 5 having an impeller position control section 4 including electromagnets 41 for attracting the impeller 21; and a control unit 6.

The present applicant has proposed a hydrodynamic bearing pump in Japanese Patent Laid-open No. 2003-201992 (corresponding to U.S. Pat. No. 6,840,735). This centrifugal type liquid pump device 1 includes: a pump section 2 having an impeller 21 rotated inside a housing 20; a body section 5 including a rotor 31 having impeller attracting magnets 33, a motor 34 for rotating the rotor 31, electromagnets 41 for attracting the impeller 21, an impeller position detecting sensor 42, and hydrodynamic grooves 38 formed in the inside surface of the housing 20; and a control mechanism 6.

For more information, refer to Japanese Patent Laid-open Nos. 2003-210572(corresponding to U.S. Pat. No. 7,033,147), 2005-270345(corresponding to U.S. Patent Application Publication No. 2005/287022), and 2005-287598 (corresponding to U.S. Patent Application Publication No. 2005/287022).

SUMMARY

In the case of both the magnetic bearing type devices and the hydrodynamic bearing type devices, it is desirable to enlarge the distance between the impeller and the blood chamber wall surface when the impeller is levitated. In the case of the magnetic bearing type devices, it is also desirable to reduce the electric power consumed by the electromagnets. To address these points, the attractive force (or repulsive force) of the permanent magnets may in some cases be reduced. In such a case, the force with which the impeller is fixed to the blood chamber in a non-operating state would be also weakened.

Thus, although it is possible to fix the impeller of the blood pump by the magnets provided in the pump, there are additional concerns. If the impeller is not positionally fixed with a force sufficiently strong to endure vibrations and impacts during storage and transportation of the blood pump, the impeller will undesirably come into contact with the blood chamber of the pump, possibly damaging the surface of the blood chamber and possibly leading to the generation of thrombus during operation of the blood pump.

In addition, there is a type of blood pump in which, as a motor for rotating an impeller, use is made of stator coils, particularly, slotless stator coils for reducing the attractive force so as to facilitate the levitation of the impeller by the function of hydrodynamic grooves. In the case of this type of pump, fixation of the impeller by magnetic forces is not possible.

According to one aspect, a blood pump device comprises a housing having a blood inflow port and a blood outflow port, an impeller rotatably positioned inside the housing to feed blood and provided with a magnetic body, an impeller rotating torque generating section attracting the impeller from outside the housing and rotating the impeller, a non-contact type bearing mechanism enabling rotation of the impeller in the housing in a non-contact state relative to an inside surface of the housing, and an impeller fixing member detachably mounted to the housing and preventing the impeller from moving inside the housing.

The blood pump device advantageously prevents an impeller from moving inside the housing before use and thereby inhibits, preferably prevents, the impeller and the housing inside surface from being damaged, irrespective of whether or not the blood pump device is of the type in which magnetism arising from the internal configuration of the pump device might be available to act on the impeller.

According to another aspect, a blood pump device comprises a housing having a blood inflow port and a blood outflow port, an impeller rotatably positioned inside the housing to feed blood, wherein the impeller is provided with a magnetic body, a motor positioned outside the housing and operable to rotate the impeller, a non-contact type bearing mechanism enabling rotation of the impeller in the housing in a non-contact state relative to an inside surface of the housing, a mounting section detachably mounted on the housing, and an entering section extending from the mounting section, with the entering section passing through the blood inflow port into the housing and engaging the impeller to fix the impeller against movement.

In accordance with another aspect, a blood pump device comprises a housing having two blood ports, with one of the ports being a blood inflow port and the other port being a blood outflow port, an impeller rotatably positioned inside the housing to feed blood, wherein the impeller being provided with a magnetic body, a motor positioned outside the housing and operable to rotate the impeller, a non-contact type bearing mechanism enabling rotation of the impeller in the housing in a non-contact state relative to an inside surface of the housing, and means for fixing the impeller against movement. The means for fixing comprises a mounting section detachably mounted on the housing, an entering section extending from the mounting section and either surrounding a portion of the housing or passing through one of the two blood ports, and a magnet provided on the entering section.

BRIEF DESCRIPTION OF THE DRAWING FIGURES

DETAILED DESCRIPTION

Figure 1:
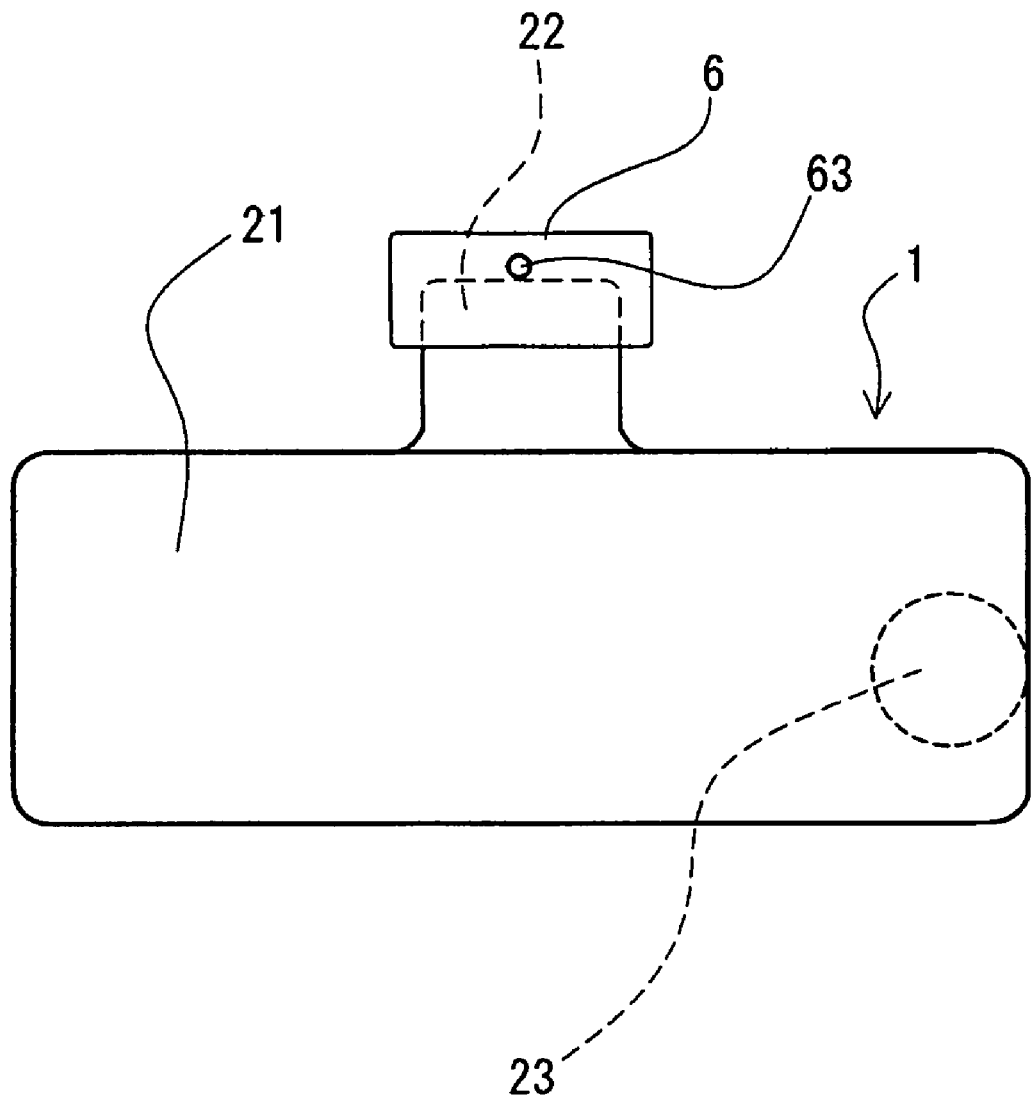
FIG. 1 is a front view of an embodiment of the blood pump device disclosed herein.

Generally speaking, the blood pump device 1 according to several of the embodiments disclosed includes: a housing 21 having a blood inflow port 22 and a blood outflow port 23; an impeller 5 having a magnetic body (first magnetic body) 25 and rotated inside the housing 21 in a non-contact state relative to an inside surface of the housing 21 so as to feed blood; an impeller rotating torque generating section 3 for attracting the impeller 5 from the outside of the housing 21 and rotating the impeller 5; and an impeller position control section 4, forming at least a part of a non-contact type bearing mechanism, enabling rotation of the impeller 5 inside the housing 21 in the non-contact state. The blood pump device 1 further includes an impeller fixing member 6 (impeller fixing means) which is detachably attached to the housing 21 and which prevents the impeller 5 from moving inside the housing 21.

With respect to the embodiment of the blood pump shown in FIGS. 1-6, the blood pump device 1 includes: the centrifugal type blood pump section 2 including the housing 21 having the blood inflow port 22 and the blood outflow port 23, and the impeller 5 rotated in the housing 21 so as to feed blood by a centrifugal force generated at the time of rotation; the impeller rotating torque generating section (non-control type magnetic bearing component section) 3 for the impeller 5; and the impeller position control section (control type magnetic bearing component section) 4 for the impeller 5.

In the blood pump device 1 according to this embodiment, the impeller rotating torque generating section 3 comprises a stator coil type motor having a plurality of stator coils arranged in a circle so as to attract the magnetic body 25 of the impeller 5 from one side of the impeller 5 and rotate the magnetic body 25 upon being electrically energized. The non-contact type bearing mechanism includes, at least in part, a magnetic member 29 provided at an upper shroud, or adjacent the upper surface, of the impeller 5 and an electromagnet 41 for attracting the magnetic member 29 of the impeller 5 in a direction opposite to the impeller rotating torque generating section 3.

Figure 3:
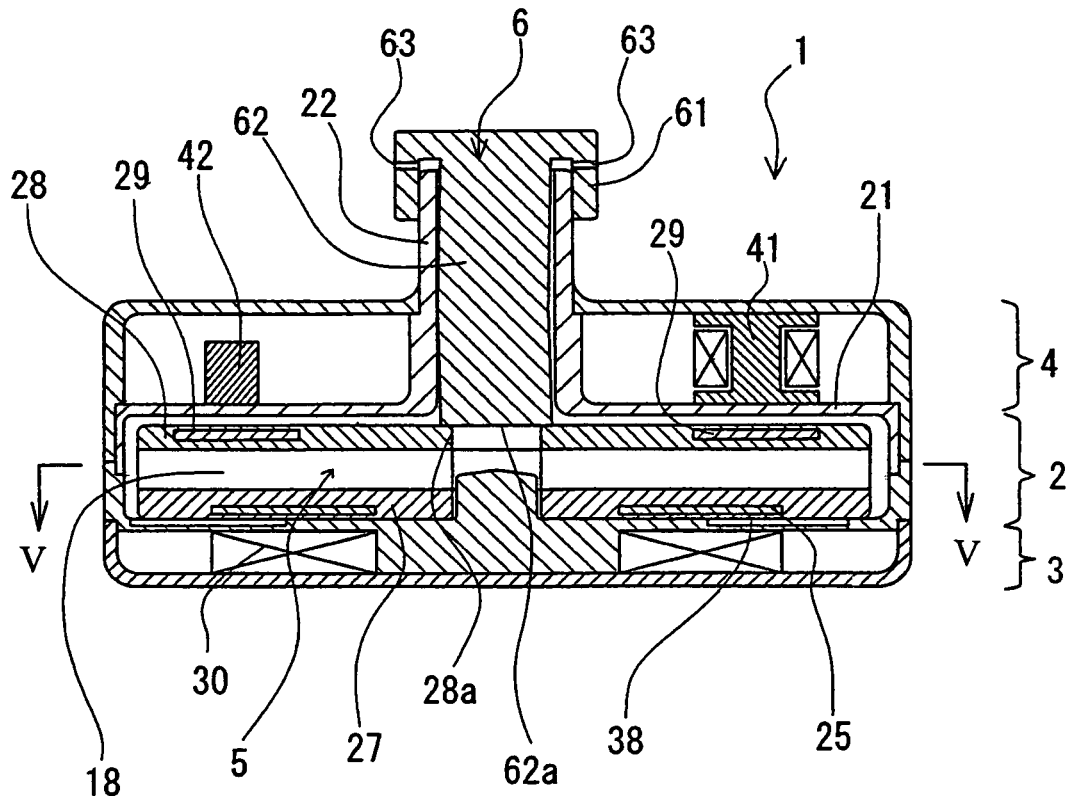
FIG. 3 is a cross-sectional view taken along the section line III-III of FIG. 2.
Figure 4:
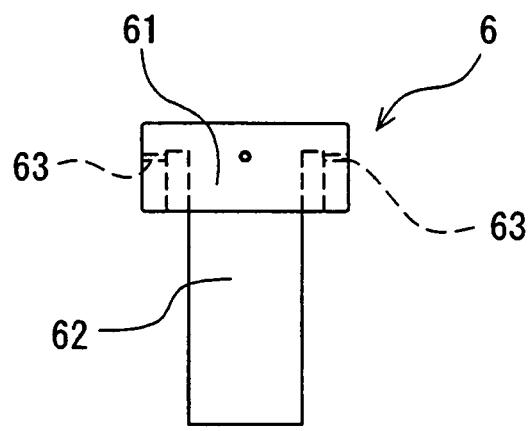
FIG. 4 is a front view of an impeller fixing member used in the blood pump device shown in FIGS. 1-3.

As shown in FIG. 3, the impeller 5 is held at a predetermined position inside the housing 21 and is normally rotated without making contact with the inside surface of the housing 21, under the actions of the non-control type magnetic bearing component section 3 and the control type magnetic bearing component section 4.

As mentioned, the blood pump device 1 here includes the blood pump section 2 including the housing 21 having the blood inflow and outflow ports 22, 23, the impeller 5 provided therein with the magnetic body 25 and the second magnetic member (a member formed of a magnetic material or a second magnetic body) 29 which is rotated inside the housing 21 to feed blood through rotation, the impeller rotating torque generating section 3 comprising a motor 30 for attracting and rotating the magnetic body 25 of the impeller 5 of the blood pump section 2, and the impeller position control section 4 comprising the electromagnet 41 for attracting the impeller 5 (specifically, the electromagnet 41 for attracting the second magnetic member 29 provided in the impeller 5) and a position sensor 42 for detecting the position of the impeller 5 (specifically, a position sensor for detecting the position of the magnetic member 29 provided in the impeller 5).

In the pump device 1 according to this embodiment, the centrifugal type blood pump section 2 includes the housing 21 and the impeller 5 contained in the housing 21.

The housing 21 has the blood inflow port 22 and the blood outflow port 23, and is formed of a non-magnetic material. The housing 21 is provided therein with a blood chamber which communicates with the blood inflow port 22 and the blood outflow port 23. The impeller 5 is contained in the housing 21. The blood inflow port 22 projects from a position near the center of the upper surface of the housing 21. As shown in FIGS. 1, 2, 5 and 6, the blood outflow port 23 is positioned to project in the tangential direction from a side surface of the housing 21 which is formed in a substantially hollow cylindrical shape.

Figure 5:
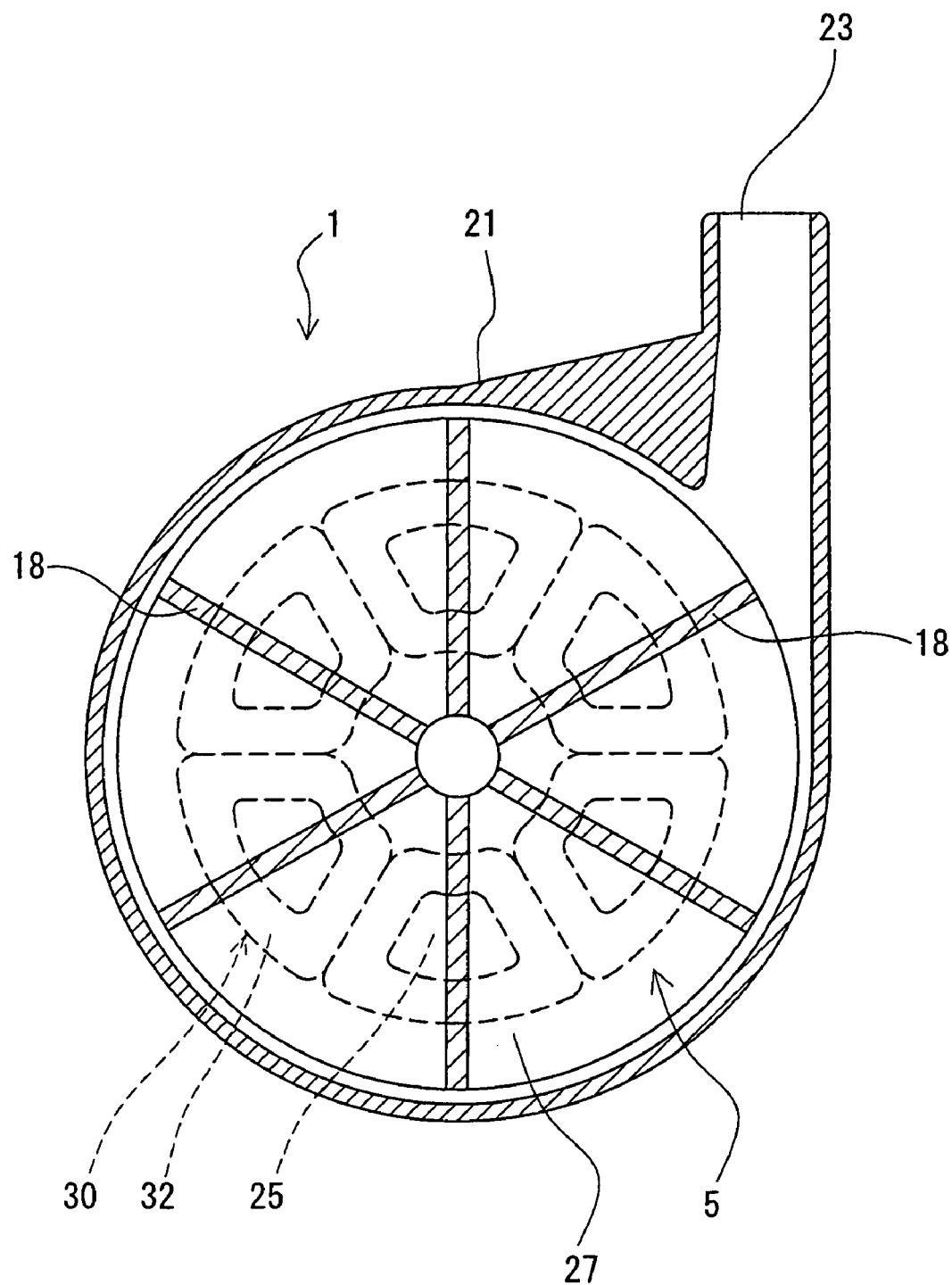
FIG. 5 is a cross-sectional view taken along the section line V-V of FIG. 3.

As shown in FIG. 3, the disk-shaped impeller 5 has a centrally located through-hole and is contained in the blood chamber formed inside the housing 21. As shown in FIGS. 3 and 5, the impeller 5 includes an annular plate-like member or lower shroud 27 having an opening at its center and forming a lower surface, an annular plate-like member or upper shroud 28 having an opening in its center and forming an upper surface, and a plurality of (for example, six) vanes 18 formed between the lower and upper shrouds 27, 28. A plurality of (for example, six) blood passages are formed between the lower shroud 27 and the upper shroud 28. Each adjacent pair of blood passages is separated or partitioned from one another by one of the vanes 18. As shown in FIG. 5, the blood passages communicate with the central opening of the impeller 5, and extend starting from the central opening of the impeller 5 to the outer peripheral edge so as to become gradually broader in width. In other words, the vanes 18 are each formed between the adjacent blood passages which contain blood during operation of the pump. Incidentally, in this embodiment, the blood passages and the vanes 18 are provided at regular equal angular intervals and in substantially the same shapes.

As shown in FIG. 5, the impeller 5 has a plurality of (for example, six) magnetic bodies 25 (permanent magnets or driven magnets) that are embedded in the impeller. In this embodiment, the magnetic bodies 25 are embedded in the lower shroud 27. The embedded magnetic bodies 25 help ensure that the impeller 5 is pulled toward the side opposite to the blood inflow port 22 by the impeller rotating torque generating section 3, which is described in more detail below, and that a rotating torque is transmitted from the impeller rotating torque generating section 3.

By providing a sufficient number of the embedded magnetic bodies 25 as in this embodiment, magnetic coupling between the impeller and the impeller rotating torque generating section 3 can be secured sufficiently. The shape of the magnetic bodies 25 is preferably a roughly trapezoidal shape as shown in FIG. 5. Alternatively, a ring-shaped magnet may be polarized into a multiplicity of poles (for example, 24 poles). In other words, a plurality of small magnets may be arranged in a circle so that positive and negative poles are alternately arranged.

In addition, the impeller 5 has a magnetic member which can be constituted by the upper shroud 28 itself or by a magnetic member provided in the upper shroud 28. In this embodiment, the magnetic member 29 is embedded in the upper shroud 28. The magnetic member 29 attracts the impeller 5 to the blood inflow port 22 side by electromagnets 41 in the impeller position control section, described in more detail below. Magnetic stainless steel or the like can be used as the magnetic member 29.

In this illustrated embodiment, the impeller position control section 4 and the impeller rotating torque generating section 3 constitute a non-contact type magnetic bearing, by which the impeller 5 is pulled (acted upon) in opposite directions so that the position of the impeller 5 is stabilized inside the housing 21 at an appropriate position so that the impeller does not make contact with the inside surface of the housing 21 and is rotated inside the housing 21 in a non-contact state.

Figure 2:
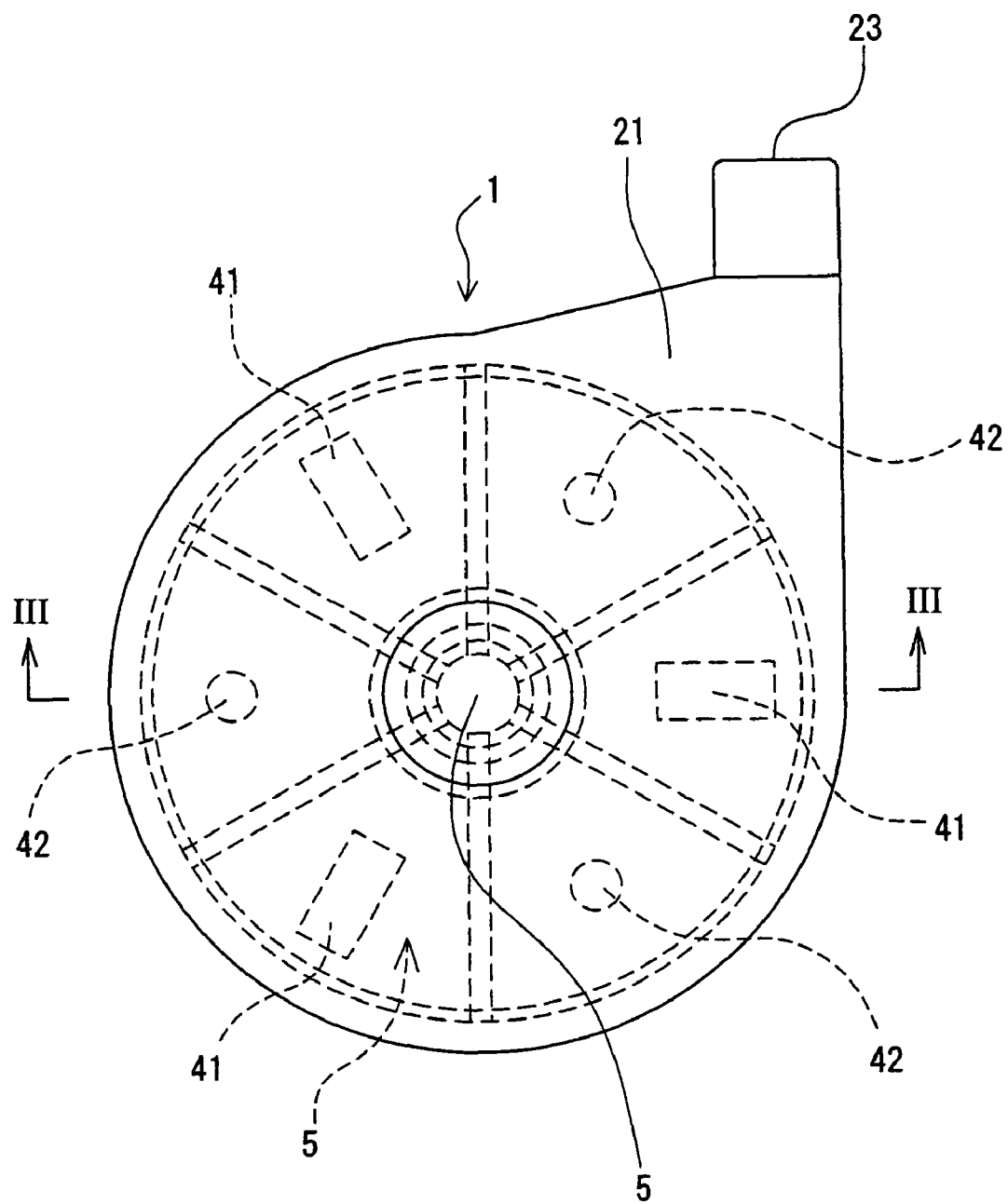
FIG. 2 is a plan view of the blood pump device shown in FIG. 1.

As shown in FIGS. 2 and 3, the impeller position control section 4 forming a part of the non-contact type bearing mechanism includes the plurality of fixed electromagnets 41 for attracting the magnetic member 29 of the impeller 5, and position sensors 42 for detecting the position of the magnetic member 29 of the impeller 5. Specifically, the impeller position control section 4 includes the plurality of the electromagnets 41 contained in the blood pump device, and the plurality of position sensors 42. In this illustrated and disclosed embodiment, three electromagnets 41 and three position sensors 42 are provided. The plurality of electromagnets 41 and the plurality of position sensors 42 of the impeller position control section 4 are provided at equal angular intervals, respectively, and the angular intervals between the electromagnets 41 and the position sensors 42 are also equal. The electromagnets 41 each include an iron core and a coil. In this embodiment, three electromagnets 41 are provided. The number of electromagnets 41 is preferably not less than three. For example, four electromagnets may be provided. The electromagnetic forces of the three or more electromagnets 41 are regulated by use of the results of detection by the position sensors 42, whereby the forces in the direction of the rotating axis (z-axis) of the impeller 5 can be balanced, and the moments about the x-axis and the y-axis (which are orthogonal to the rotating axis (z-axis)) can be controlled.

The position sensors 42 detect the spacing between the electromagnet 41 and the magnetic member 29, and their detection outputs are sent to a control unit of a control mechanism for controlling the current or voltage supplied to each of the coils of the electromagnets 41. In the illustrated embodiment, the fixed electromagnets 41 and the position sensors 42 are positioned on the upper side of the housing 21 and are enclosed within a space covered by a cover that is connected to the housing as shown by way of example in FIG. 3.

In the pump device 1 according to this embodiment, as shown in FIG. 5, the impeller rotating torque generating section 3 forming a part of the non-contact type bearing mechanism includes a stator coil type motor 30 having a plurality of stator coils 32 which are contained in the blood pump device and are arranged in a circle so as to attract and rotate the magnetic bodies 25 of the impeller 5 from one side of the impeller 5 upon being electrically energized. In the illustrated embodiment, the motor 30 is positioned on the lower side of the housing 21 and is enclosed within a space covered by a cover that is connected to the housing as shown by way of example in FIG. 3.

The stator coils 32 are arranged on the circumference of a circle at substantially equal angular intervals about the center (axis) of the circle. Specifically, six stator coils are provided in this embodiment. As the stator coils, multilayer wound stator coils are used. By switching the direction of the current passed to each of the stator coils 32, a rotating magnetic field is generated, whereby the impeller is attracted and rotated.

As shown in FIG. 5 and mentioned above, a plurality of magnetic bodies 25 which are permanent magnets that serve as magnets for coupling, are embedded in the impeller 5. Though FIG. 5 illustrates six magnetic bodies 25, the number is not limited in that regard. For example, six to twelve magnetic bodies can be provided. In this embodiment, the magnetic bodies 25 are embedded in the lower shroud 27. The magnetic bodies 25 embedded in the impeller 5 are attracted toward the side opposite to the blood inflow port 22 by the stator coils 32 of the impeller rotating torque generating section 3, are coupled to the operations of the stator coils 32, and transmit a rotating torque to the impeller 5.

In addition, by embedding a certain number of magnetic bodies 25 as in this embodiment, the magnetic coupling with the stator coils 32 described in more detail below can be secured sufficiently. As mentioned, the shape of the magnetic bodies 25 is preferably roughly trapezoidal, although the magnetic bodies 25 may also be ring-like or plate-like. Preferably, the number and layout of the magnetic bodies 25 corresponds to the number and layout of the stator coils 32. Preferably, the plurality of magnetic bodies 25 are disposed on the circumference of a circle so that their polarities vary alternately and they are at substantially regular angular intervals about the center axis of the impeller 5.

In addition, the blood pump device 1 in this embodiment is a centrifugal type blood pump device, and, as shown in FIG. 3, the housing 21 has a blood passage extending from the blood inflow port 22. As also shown in FIG. 3, the impeller 5 has a central opening part located on an extension line of the blood passage. In the blood pump device 1 of this embodiment, in the absence of electrical energization, the motor 30 and the electromagnets 41 have no magnetic force and, therefore, they do not attract the impeller 5. Accordingly, this device is of the type in which the impeller 5 can move freely inside the housing 21 when electrical energization is not being performed.

However, the blood pump device 1 in this embodiment includes the impeller fixing member 6, which prevents the impeller 5 from moving inside the housing 21. The impeller fixing member 6 in this embodiment includes a detachable mounting section 61 adapted to be mounted to the blood inflow port 22, and an impeller fixing section 62 extending from the mounting section 61. This impeller fixing section 62 is positioned in the blood inflow port 22, and is operative to fix the impeller 5 by pressing the impeller 5 against the inside surface of the housing 21. In this embodiment, the impeller fixing section 62 of the impeller fixing member 6 includes an impeller pressing part 62a that presses against the peripheral edge portion of the central opening part 28a of the impeller 5.

More specifically, in the blood pump device 1, as shown in FIG. 3, the aperture diameter of the central opening part 28a of the impeller 5 is slightly smaller than the inside diameter of the blood passage extending from the blood inflow port 22. In addition, the impeller fixing member 6 includes the mounting section 61 capable of being detachably mounted to the blood inflow port 22, and the impeller fixing section 62 extending from the mounting section 61. The impeller fixing section 62 is formed of an elastic material, and the tip surface of the fixing section 62 presses the peripheral edge portion of the central opening part 28a of the impeller 5. To be more specific, the impeller fixing section 62 is formed in a solid cylindrical or hollow cylindrical shape from an elastic material, with its overall outer diameter being smaller than the inside diameter of the blood passage extending rectilinearly from the blood inflow port 22, and with the outer diameter of at least its tip being slightly larger than the aperture diameter of the central opening part 28a of the impeller 5. Therefore, the impeller fixing section 62 extends into the blood passage through the blood inflow port 22 and presses against the impeller 5. In other words, the tip surface of the impeller fixing section 62 constitutes the impeller pressing part. When made of an elastic material, the impeller fixing section 62 not only presses the impeller 5, but also elastically deforms and thus does not damage the impeller 5.

The mounting section 61 of the impeller fixing member 6 may be of any form allowing it to be detachably mounted to the blood inflow port 22. In this embodiment, the mounting section is a cap-like section capable of fitting to the outside surface of the blood inflow port 22. In addition, the mounting section 61 of the impeller fixing member 6 in this embodiment is mounted to the blood inflow port 22 in a substantially gas-tight manner, and has a sterilizing gas passage 63 permitting a sterilizing gas to enter therethrough into the inside of the housing 21. In the device as shown in FIGS. 1 and 3, a plurality of the sterilizing gas passages 63 are provided at a side surface. However, the sterilizing gas passages may be formed in other ways. The sterilizing gas passages may be formed by use of a configuration in which the mounting section 61 of the impeller fixing member 6 is not mounted to the blood inflow port 22 in a gas-tight state. For example, the sterilizing gas passages may be formed by providing the inside surface of the mounting section 61 of the impeller fixing member 6 with ribs. In addition, the impeller fixing section 62 is so formed as not to make close contact with the inside surface of the blood passage and not to close the passage (i.e., a space exists between the outer surface of the fixing section and the inner surface of the inflow port 22. Therefore, the impeller fixing member 62 does not hinder the sterilizing gas from flowing.

An impeller fixing force F exerted by the impeller fixing member 62 on the impeller 5 may generally be as follows. Movements of the impeller 5 upon vibrations or impact loads during storage and transportation can be securely suppressed when the following condition is satisfied:

$$F > ma,$$

where F is the impeller fixing force, m is the mass of the impeller 5, and a is an expected acceleration of disturbance.

In addition, the material forming the impeller fixing section 62 may be any material having a certain amount of flexibility or elasticity. Examples of the material which can be used to form the impeller fixing section 62 include olefin-based elastomers (polyethylene elastomer, polypropylene elastomer), amide-based elastomers (polyamide elastomer), styrene-based elastomers (e.g., styrene-butadiene-styrene copolymer, styrne-isoprene-styrene copolymer, styrene-ethylenebutylene-styrene elastomer), polyurethane, urethane-based elastomer, synthetic rubbers such as urethane rubber, silicone rubber, butadiene rubber, etc., natural rubbers such as latex rubber, etc., and soft polyvinyl chloride. While the mounting section 61 and the impeller fixing section 62 are formed as one body in the impeller fixing member 6 shown in FIG. 3, they may be formed as separate members and from different materials.

Figure 6:
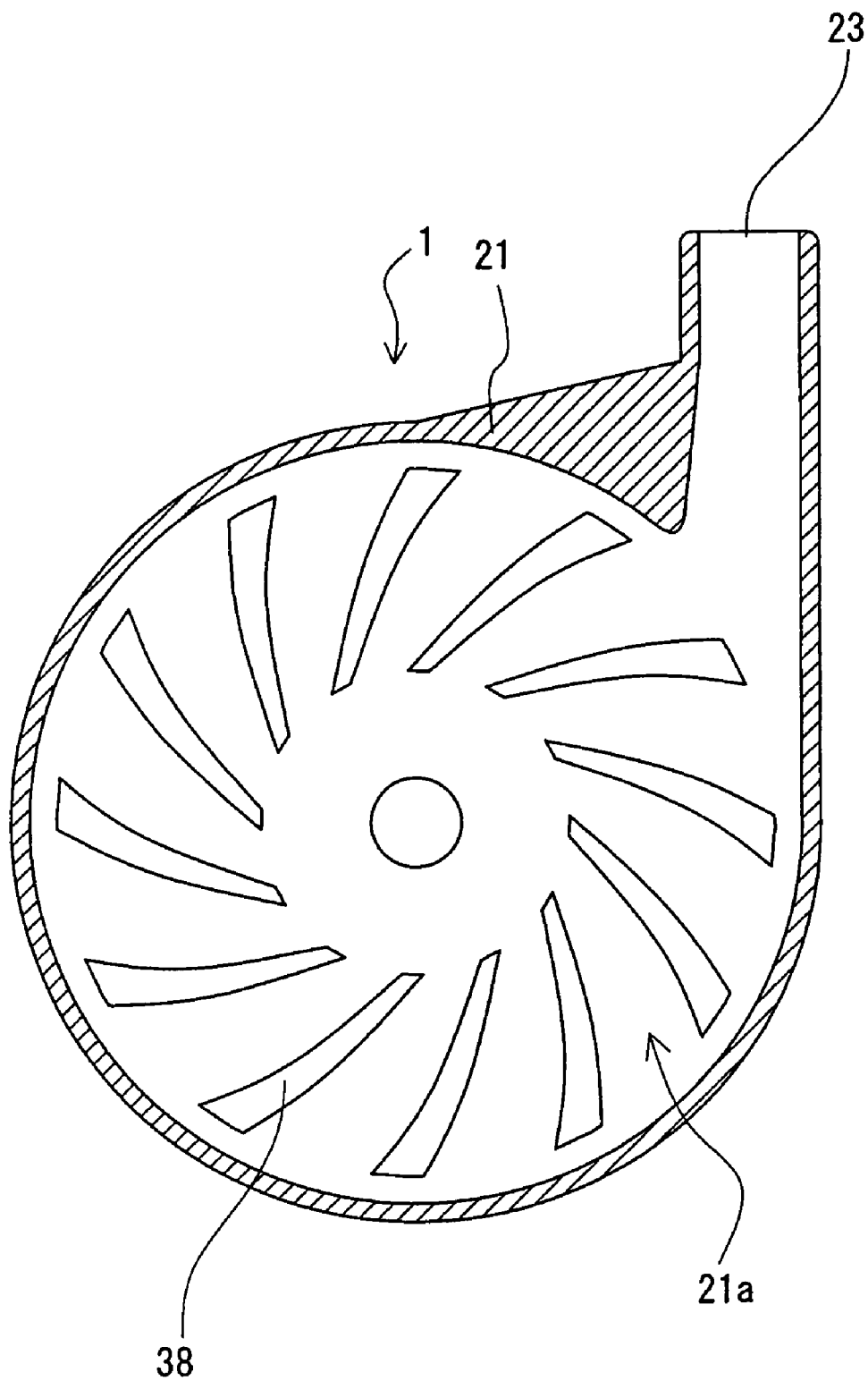
FIG. 6 is a cross-sectional view showing the condition where an impeller is removed from the condition shown by the cross-sectional view taken along the section line V-V of FIG. 3.

In addition, in the centrifugal type blood pump device 1 in this embodiment, as shown in FIG. 6, the housing 21 has a housing inside surface for containing the impeller 5 therein and forming the blood chamber, and has first hydrodynamic grooves 38 (hydrodynamic pressure generating means) provided in the housing inside surface 21a on the side of the motor 30 for generating hydrodynamic pressure. The impeller 5 can be rotated in a non-contact state by a hydrodynamic bearing effect produced between the impeller 5 and the hydrodynamic grooves 38 due to the rotation at a rotating speed of not less than a predetermined value in the condition where the operation of the electromagnets 41 is stopped. In the blood pump device of the type in this embodiment, the hydrodynamic grooves need not necessarily be provided.

Figure 7:
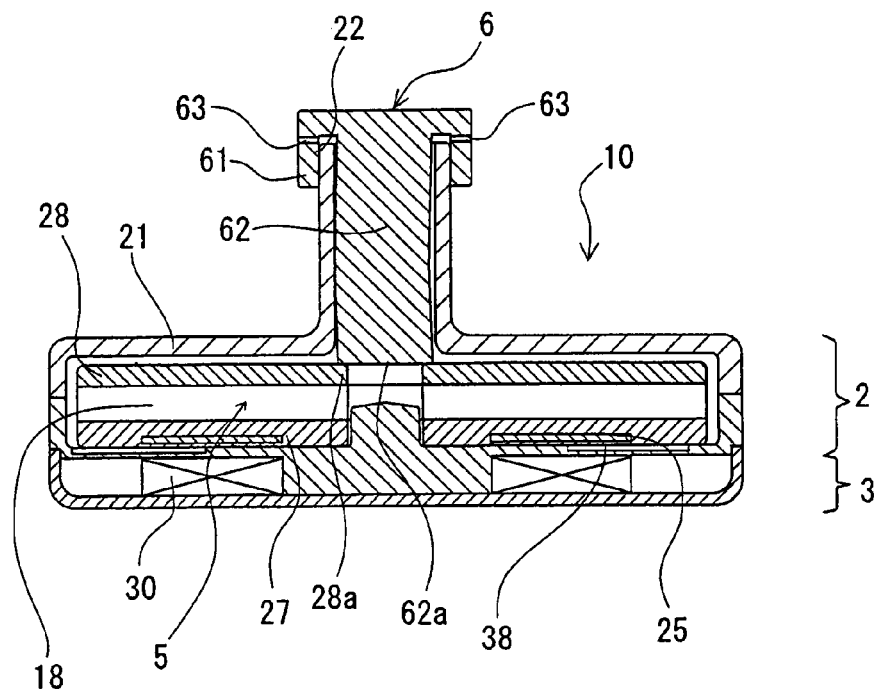
FIG. 7 is a cross-sectional view of another embodiment of the blood pump device disclosed herein.

In addition, the blood pump device may be of the type as shown in FIG. 7. The blood pump device 10 in this embodiment differs from the blood pump device 1 in the above-described embodiment in that it does not have an impeller position control section including electromagnets 41 and position sensors 42, and that a non-contact type bearing mechanism includes hydrodynamic grooves 38 provided in the housing inside surface 21a, on the motor 30 side, of the housing inside surface for containing the impeller 5 and forming the blood chamber, as shown in FIG. 6.

In this blood pump device 10, an impeller rotating torque generating section 3 is a stator coil type motor including a plurality of stator coils arranged in a circle so as to attract and rotate magnetic bodies 25 of an impeller 5 from one face side of the impeller 5 when electrically energized. The non-contact type bearing mechanism includes the hydrodynamic grooves 38 formed in the housing inside surface on the side of the impeller rotating torque generating section 3. The impeller 5 is rotated in a non-contact state by the hydrodynamic bearing effect produced between the impeller 5 and the hydrodynamic grooves 38 due to rotation at a rotating speed of not less than a predetermined value. Also, in the blood pump device of the type in this embodiment, the impeller fixing member 6 of the type described above can be used. In addition, in the blood pump device according to this embodiment, in the state in which the motor 30 is not electrically energized, the motor 30 does not attract the impeller 5 because it does not have a magnetic force. In such a condition, therefore, the impeller 5 can move freely inside the housing 21.

Figure 8:
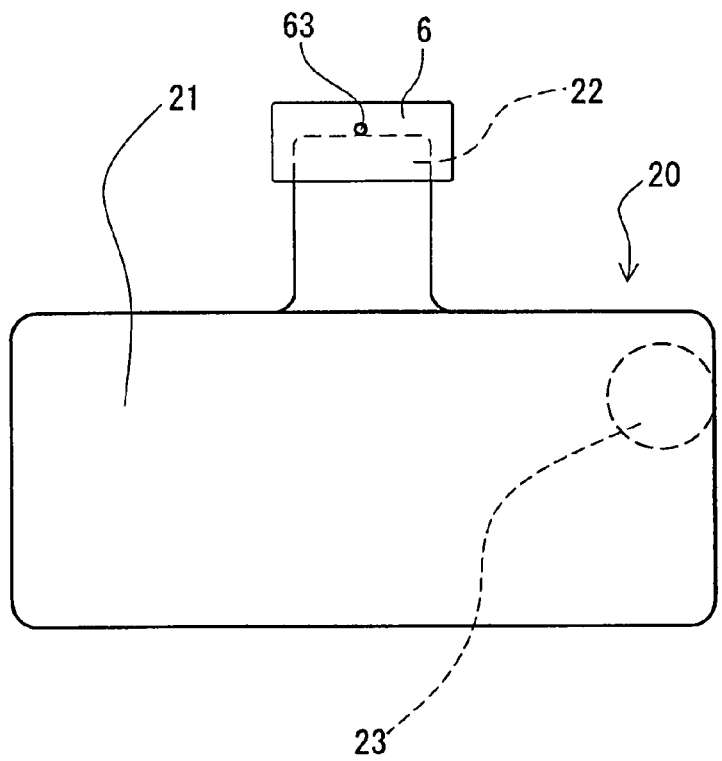
FIG. 8 is a front view of a further embodiment of the blood pump device disclosed herein.
Figure 9:
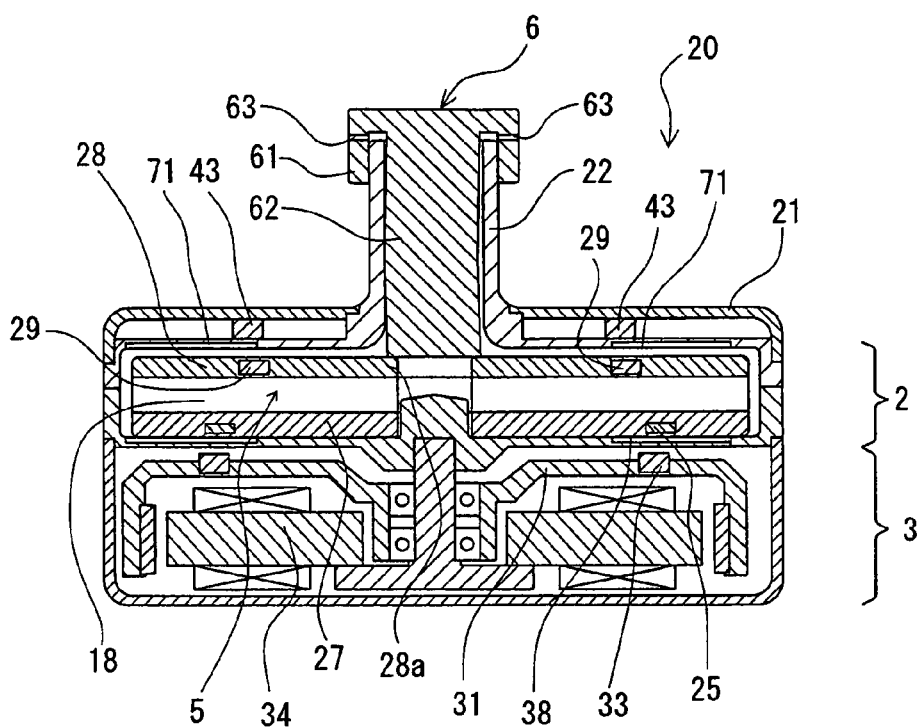
FIG. 9 is a cross-sectional view of the blood pump device shown in FIG. 8.

The blood pump device may be of another type as shown in FIGS. 8 and 9. The blood pump device 20 according to this embodiment differs from the blood pump device 1 in the above-described FIG. 1 embodiment in that it does not have an impeller position control section including electromagnets 41 and position sensors 42, that a non-contact type bearing mechanism includes hydrodynamic grooves 38 provided in the housing inside surface 21a, on the motor 30 side, of the inside surface of the housing containing the impeller 5 and forming a blood chamber as shown in FIG. 6, that an impeller rotating torque generating section 3 is a motor of the type including a rotor having permanent magnets, and that it includes an auxiliary impeller attracting permanent magnet.

As shown in FIG. 9, in this embodiment also, the impeller 5 has a plurality of (e.g., 5 to 40) magnetic bodies 25 (permanent magnets or magnets for coupling) embedded therein. In this embodiment, the magnetic bodies 25 are embedded in a lower shroud 27 of the impeller. The magnetic bodies 25 embedded in the impeller 5 are attracted to the side opposite to a blood inflow port 22 by permanent magnets 33 provided in a rotor 31 of the impeller rotating torque generating section 3 so that a rotating torque generated by the impeller rotating torque generating section 3 is transmitted to the impeller 5.

In addition, with a certain number of the magnetic bodies 25 embedded as in this embodiment, magnetic coupling with the rotor 31, can be secured sufficiently. The shape of the magnetic bodies 25 (permanent magnets) is preferably a circle.

As shown in FIG. 9, the impeller rotating torque generating section 3 includes the rotor 31 contained in the pump device and a motor 34 for rotating the rotor 31. The rotor 31 has a plurality of permanent magnets 33 provided in its surface on the blood pump section 2 side. The center of the rotor 31 is fixed to a rotating shaft of the motor 34. The permanent magnets 33 are provided in plural and at regular or equal angular intervals so as to correspond to the layout conditions (the number and positions) of the permanent magnets 25 of the impeller 5.

In this blood pump device 20, an impeller position control section including electromagnets 41 and position sensors 42 is not provided. The non-contact type bearing mechanism includes hydrodynamic grooves 38 provided in the housing inside surface 21a, on the motor side, of the housing containing the impeller 5 and forming a blood chamber in a manner similar to that shown in FIG. 6. The impeller 5 is rotated in a non-contact state by a hydrodynamic bearing effect produced between the impeller 5 and the hydrodynamic grooves 38 due to rotation at a rotating speed of not less than a predetermined value.

Further, in the blood pump device 20 in this embodiment, as shown in FIG. 9, the impeller 5 includes second magnetic members 29 embedded in an upper shroud 28 of the impeller and provided separately from the magnetic bodies 25. Also provided is a fixed permanent magnet or magnets 43 for attracting the second magnetic members 29 in the direction opposite to the motor side. The permanent magnet(s) 43 may be an annular magnet or a plurality of arcuate magnets. The impeller 5 is attracted in opposite directions by both the permanent magnets 33 of the rotor 31 and the permanent magnet(s) 43. The plurality of permanent magnets are arranged at regular or equal angular intervals about the center of the impeller 5. The number of permanent magnet(s) 43 is preferably one or more, for example, in the range of two to six.

Furthermore, in the blood pump device 20 in this embodiment, it is preferable to include second hydrodynamic grooves 71 at the inside surface of the housing 21, on the side of the housing adjacent the permanent magnet 43 or provided on the surface of the impeller 5 facing towards the permanent magnet 43 (i.e., the permanent magnet 43 side of the impeller 5).

In the blood pump device 20 in this embodiment, the impeller 5 is attracted in two opposite directions, i.e., toward the motor side and toward the blood inflow port side. Therefore, as far as there is no considerable difference between the two attracting forces, the position of the impeller 5 could potentially be instable, and the impeller 5 may quite possibly move inside the housing 21. In the blood pump device of the type in this embodiment, also, an impeller fixing member 6 of the type described above can be provided.

Figure 10:
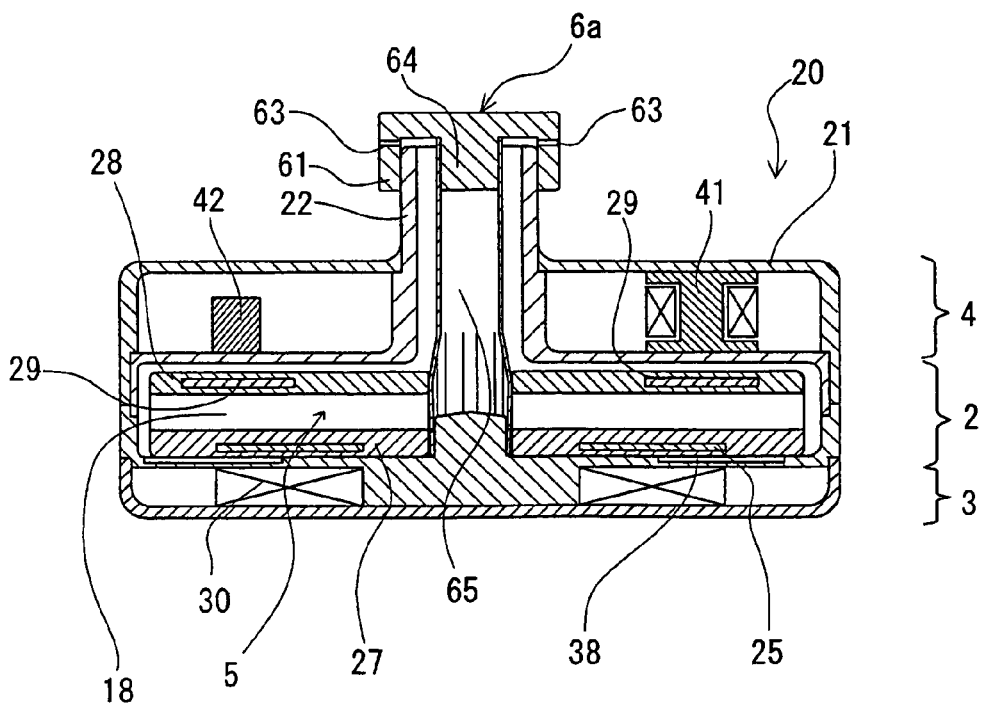
FIG. 10 is a cross-sectional view of yet another embodiment of the blood pump device disclosed herein.
Figure 11:
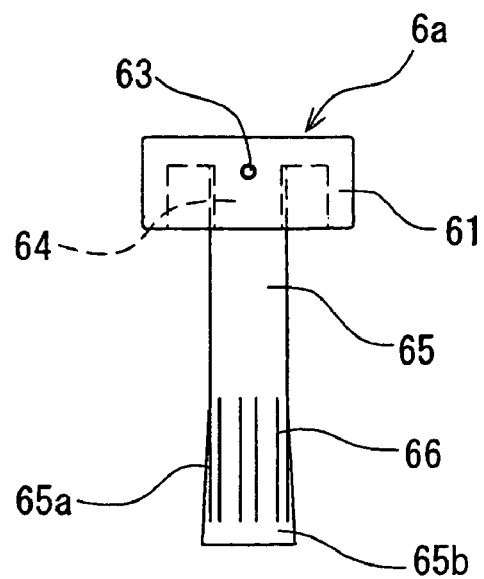
FIG. 11 is a front view of an impeller fixing member used in the blood pump device shown in FIG. 10.

In addition, in all the blood pump devices of the types described above, the impeller fixing member may be of the type as shown in FIGS. 10 and 11. The impeller fixing member 6a shown in FIGS. 10 and 11 is the same in basic configuration as the above-described impeller fixing member 6.

The impeller fixing member 6a in this embodiment has an elastic tip part capable of entering into a central opening part of the impeller 5 and operative to hold the impeller 5 by elastic deformation.

More specifically, the impeller fixing member 6a includes a mounting section 61 capable of being detachably mounted to the blood inflow port, and an impeller holding section 65 extending from the mounting section 61 and positionable in the blood inflow port and operative to hold the impeller 5. The impeller holding section 65 of the impeller fixing member 6a in this embodiment has a tubular part 65a capable of extending into the central opening part 28a of the impeller 5. The tubular part 65a is provided with a plurality of slits 66 (e.g., three to ten slits) extending in the axial direction. The tubular part 65a is provided at its tip with a non-slit portion 65b in which the slits are not present. Therefore, the slits 66 extend by a predetermined length toward the base end side (upper side in FIG. 10) from a position spaced towards the base end side from the tip of the impeller holding section 65. In addition, at least the tubular part 65a of the impeller holding section 65 is formed of a material having some degrees of shape-retaining property and flexibility.

To position the fixing member 6a in place, the impeller holding section 65 is positioned to extend into the central opening part 28a of the impeller 5 where it comes into contact with the inside surface of the housing 21 as shown in FIG. 10. Upon being pressed further, the holding section 65 is deformed so as to bulge outward as also shown in FIG. 10 and makes contact with the central opening part 28a of the impeller 5, thereby holding the impeller 5. In addition, a base end part of the impeller holding section 65 is fixed to a projecting section 64 projecting from the inside surface of the mounting section 61.

The condition in which the impeller 5 is held is maintained by the fitting of the mounting section 61 of the impeller fixing member 6a to the blood inflow port 22. Besides, the impeller fixing member 6a in this embodiment is mounted to the blood inflow port 22 in a substantially gas-tight condition, and has a sterilizing gas passage 63 permitting a sterilizing gas to enter into the inside of the housing 21. As shown in FIGS. 10 and 11, a plurality of sterilizing gas passages 63 are preferably provided. In the illustrated embodiment, the sterilizing gas passages 63 are provided in or extend through the side surface of the mounting section 61. The sterilizing gas passages may alternatively be formed by use of a structure in which the mounting section 61 of the impeller fixing member 6a is mounted to the blood inflow port 22 in a non-gas-tight condition. For example, the sterilizing gas passages may be formed by providing the inside surface of the mounting section 61 of the impeller fixing member 6a with ribs. In addition, the impeller holding section 65 does not make close contact with the inside surface of the blood passage and, hence, does not close up the passage. Therefore, the impeller holding section 65 does not hinder the flow of the sterilizing gas.

The material forming the impeller holding section 65 may be any material that has some degrees of flexibility and shape-retaining property. Examples of materials which can be used to form the impeller holding section 65 include polyolefins (polyethylene, polypropylene, ethylene-propylene copolymer), styrene-based resins [polystyrene, MS resin (methacrylate-styrene copolymer), MBS resin (methacrylate-butylene-styrene copolymer)], and polyamides (6 nylon, 66 nylon).

Figure 12:
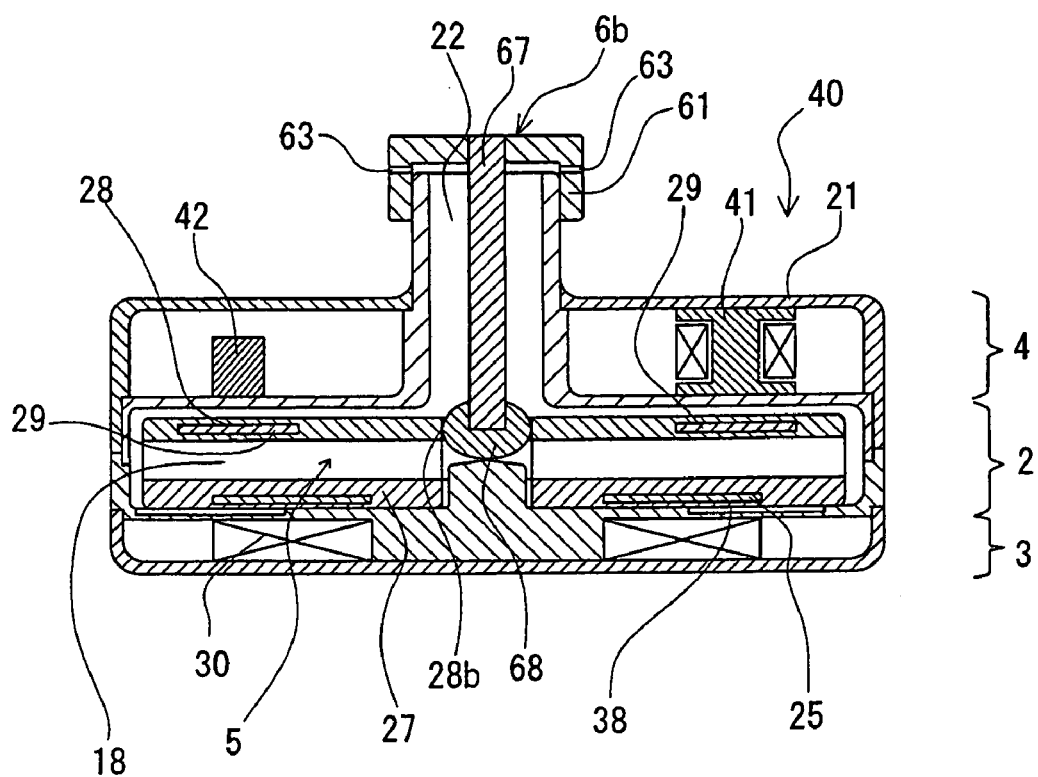
FIG. 12 is a cross-sectional view of a yet further embodiment of the blood pump device disclosed herein.
Figure 13:
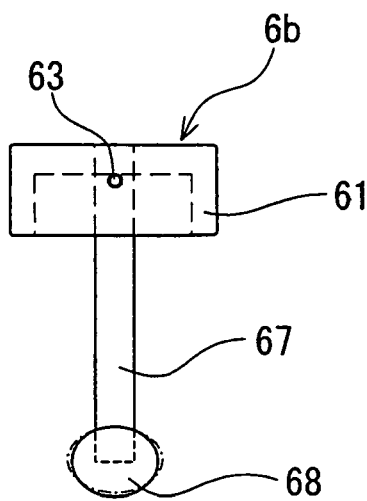
FIG. 13 is a front view of an impeller fixing member used in the blood pump device shown in FIG. 12.

In all the blood pump devices of the above-mentioned types, the impeller fixing member may be of a different type such as shown in FIGS. 12 and 13. The impeller fixing member 6b shown in FIGS. 12 and 13 is generally the same as the above-described impeller fixing member 6 in its basic configuration. However, the impeller fixing member 6b in this embodiment has an elastic tip part 68 capable of entering into the central opening part of the impeller 5 and operative to hold the impeller 5 by elastic deformation. Particularly, in this embodiment, the elastic tip part 68 is an elastic spherical part.

Specifically, the impeller fixing member 6b includes a detachable mounting section 61 for mounting to the blood inflow port, a shaft section 67 extending from the mounting section 61 and adapted to be positioned in the blood inflow port, and the elastic tip part 68 adapted to be positioned in the central opening part of the impeller 5. While the elastic tip part 68 is an elastic spherical part in this embodiment, it may alternatively be an elastic frustoconical part with a tip small in diameter. It is to be understood that the shaft section 67 and the elastic tip part 68 may be formed integrally in one piece as a single body rather than as separate parts.

In a non-pressed state (solid line in FIG. 13), the elastic tip part 68 is so shaped that it can enter into the central opening part of the impeller 5. After the elastic tip part 68 enters into the central opening part of the impeller 5 and makes contact with the inside surface of the housing 21, it is pressed further, whereby it is somewhat compressed and enlarged in outer diameter as shown in FIG. 12 (broken line in FIG. 13), to come into close contact with the central opening part of the impeller 5, thereby holding the impeller 5. The condition in which the impeller 5 is held is maintained by the fitting of the mounting section 61 of the impeller fixing member 6b to the blood inflow port 22.

In addition, the impeller fixing member 6b in this embodiment is mounted to the blood inflow port 22 in a substantially gas-tight condition, and has a sterilizing gas passage 63 permitting a sterilizing gas to enter into the inside of the housing. As shown in FIGS. 12 and 13, several sterilizing gas passages 63 are preferably provided, and in the illustrated version are provided in a side surface of the mounting section 61. Also, as mentioned previously, the sterilizing gas passages 63 may be formed by use of a structure in which the mounting section 61 of the impeller fixing member 6b is mounted to the blood inflow port 22 in a non-gas-tight condition. For example, the sterilizing gas passages may be formed by providing ribs on the inside surface of the mounting section 61 of the impeller fixing member 6b.

The material forming the elastic tip part 68 may be any material that has some degree of elasticity. Examples of the material which can be used to form the elastic tip part 68 include olefin-based elastomers (polyethylene elastomer, polypropylene elastomer), amide-based elastomers (polyamide elastomers), styrene-based elastomers (e.g., styrene-butadiene-styrene copolymer, styrene-isoprene-styrene copolymer, styrene-ethylenebutylene-styrene copolymer), polyurethane, urethane-based elastomer, synthetic rubbers such as urethane rubber, silicone rubber, butadiene rubber, etc., natural rubbers such as latex rubber, etc., and soft polyvinyl chloride.

Besides, examples of the material which can be used to form the shaft section 67 include polyolefins (polyethylene, polypropylene, ethylene-propylene copolymer), styrene-based resins [polystyrene, MS resin (methacrylate-styrene copolymer), MBS resin (methacrylate-butylene-styrene copolymer)], and polyamides (6 nylon, 66 nylon).

Figure 14:
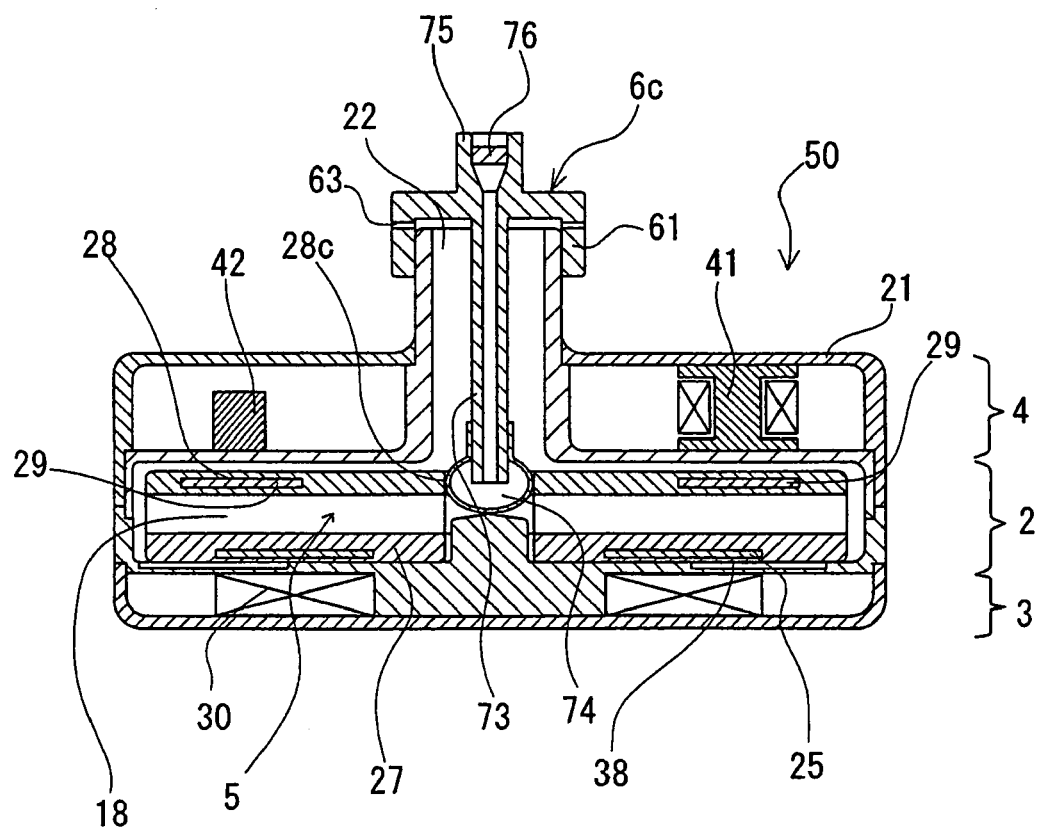
FIG. 14 is a cross-sectional view of still another embodiment of the blood pump device disclosed herein.
Figure 15:
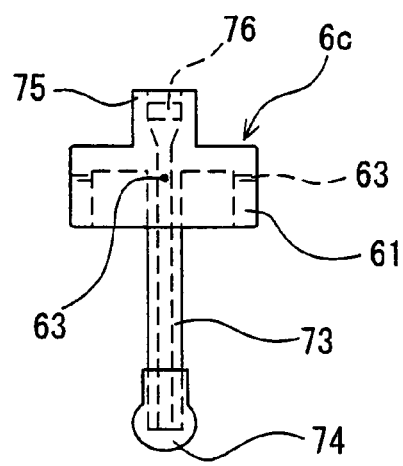
FIG. 15 is a front view of an impeller fixing member used in the blood pump device shown in FIG. 14.
Figure 16:
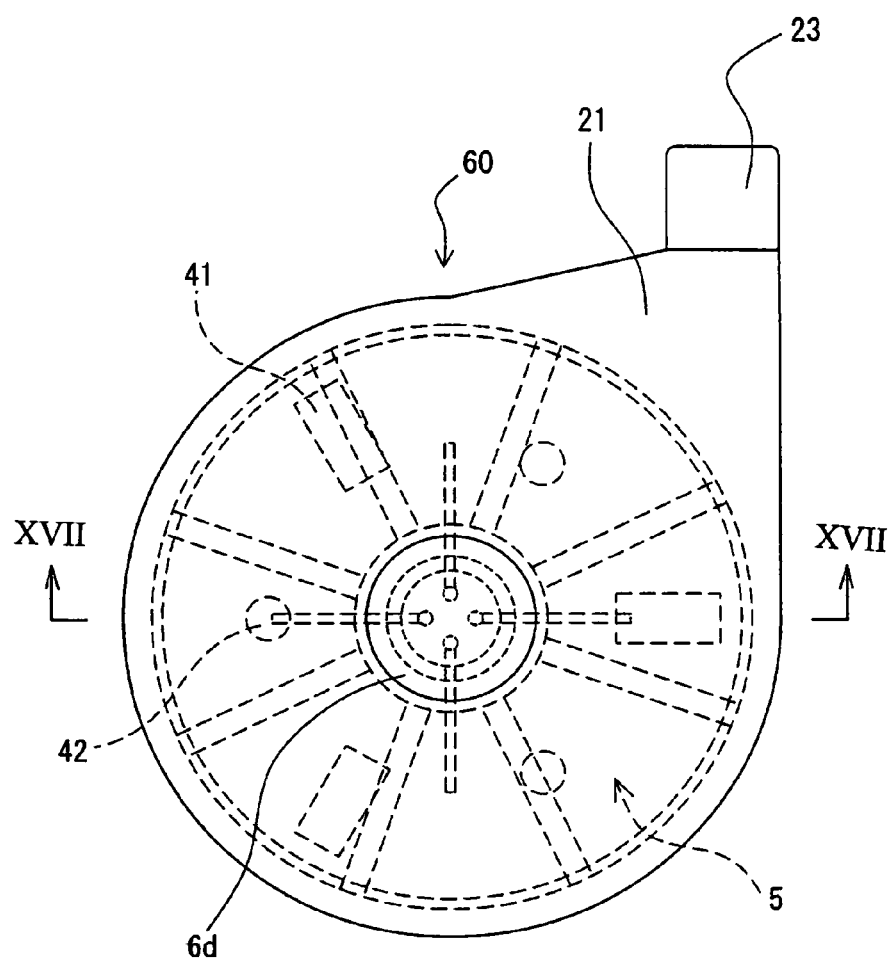
FIG. 16 is a plan view of a still further embodiment of the blood pump device disclosed herein.

In all the blood pump devices of the types described above, the impeller fixing member may be of another alternative as shown in FIGS. 14 and 15. The impeller fixing member 6c shown in FIGS. 14 and 15 is generally the same in basic configuration as the above-described impeller fixing member 6. The impeller fixing member 6c in this embodiment has an elastic tip part 74 capable of entering into a central opening part of an impeller 5 and operative to hold the impeller 5 by elastic deformation. More particularly, in this embodiment the elastic tip part 74 is a balloon which is inflated by feeding a fluid into the inside of the balloon.

Here, the impeller fixing member 6c includes a detachable mounting section 61 adapted to be mounted to a blood inflow port, a hollow shaft section 73 extending from the mounting section 61 and adapted to be positioned in the blood inflow port, and the elastic tip part 74 adapted to enter into the central opening part of the impeller 5. In this embodiment, the elastic tip part 74 is a balloon which is inflated by feeding a fluid into the inside of the balloon. It is to be understood that the shaft section and the elastic tip part may also be formed as an integral one-piece body.

Further, the mounting section 61 is provided with a fluid injector mounting port 75, and the inside of the port 75 and the inside of the balloon 74 communicate with each other through the lumen of the shaft section 73. In addition, the fluid injector mounting port 75 is equipped with a seal valve 76 which is opened when a blood injector (e.g., a syringe) is mounted to or penetrated through the valve 76, and which closes when the blood injector is not mounted to, or is separated from, the seal valve 76. Therefore, in the impeller fixing member 6c, the inflated state of the balloon is maintained after the injection of a fluid.

In a non-inflated state shown in FIG. 15, the elastic tip part 74 is shaped so that it can enter into or be positioned in the central opening part of the impeller 5. After the elastic tip part 74 enters into the central opening part of the impeller 5, a fluid (e.g., air) is injected through the fluid injector mounting port 75, whereby the balloon is inflated as shown in FIG. 14. The impeller fixing member 6c holds the impeller 5 by the close contact of the inflated balloon with the central opening part of the impeller 5. The condition in which the impeller 5 is held is maintained by the fitting of the mounting section 61 of the impeller fixing member 6c to the blood inflow port 22.

In addition, the impeller fixing member 6*c* in this embodiment is mounted to the blood inflow port 22 in a substantially gas-tight condition, and has sterilizing gas passages 63 permitting a sterilizing gas to enter into the inside of the housing. The sterilizing gas passages 63 are the same as described previously above. In addition, as also mentioned above, the sterilizing gas passages 63 may be formed by use of a structure in which the mounting section 61 of the impeller fixing member 6*c* is mounted to the blood inflow port 22 in a non-gas-tight condition. For example, the sterilizing gas passages may be formed by providing ribs at the inside surface of the mounting section 61 of the impeller fixing member 6*c*.

The material forming the elastic tip part (balloon) 74 may be any material that has some degree of elasticity. Examples of materials which can be used to form the elastic tip part 74 include olefin-based elastomers (polyethylene elastomer, polypropylene elastomer), amide-based elastomers (polyamide elastomers), styrene-based elastomers (e.g., styrene-butadiene-styrene copolymer, styrne-isoprene-styrene copolymer, styrene-ethylenebutylene-styrene copolymer), polyurethane, urethane-based elastomer, synthetic rubbers such as urethane rubber, silicone rubber, butadiene rubber, etc., natural rubbers such as latex rubber, etc., and soft polyvinyl chloride.

Examples of materials which can be used to form the shaft section 73 include polyolefins (polyethylene, polypropylene, ethylene-propylene copolymer, styrene-based resins [polystyrene, MS resin (methacrylate-styrene copolymer), MBS resin (methacrylate-butylene-styrene copolymer)], and polyamides (6 nylon, 66 nylon).

In all the blood pump devices of the types described above, the impeller fixing member may be of the type as shown in FIGS. 16-19. The impeller fixing member 6*d* shown in FIGS. 16-19 is generally similar to the above-described impeller fixing member 6 in its basic configuration.

The impeller fixing member 6*d* in this embodiment has an elastic tip part adapted to be positioned in the central opening part of an impeller 5 and operative to press the impeller 5 by elastic deformation.

The impeller 5 in the blood pump device 60, for which the impeller fixing member 6*b* in this embodiment is used, has a disk-shaped lower shroud 27. Also, in the impeller 5 shown in FIG. 17, the aperture diameter of the central opening part is larger than the inside diameter of the blood passage. However, like the blood pump devices in embodiments described above, the aperture diameter of the central opening part of the impeller 5 may be smaller than the inside diameter of the blood passage.

The impeller fixing member 6*d* includes a detachable mounting section 61 adapted to be mounted to a blood inflow port, and a plurality of string-like or strip-like elastic members (collectively referred to as elongated elastic members) extending from the mounting section 61. These elongated elastic members are adapted to extend through the blood inflow port and to press the disk-shaped lower shroud 27 by entering into the impeller 5 through the central opening part of the impeller 5.

Figure 18:
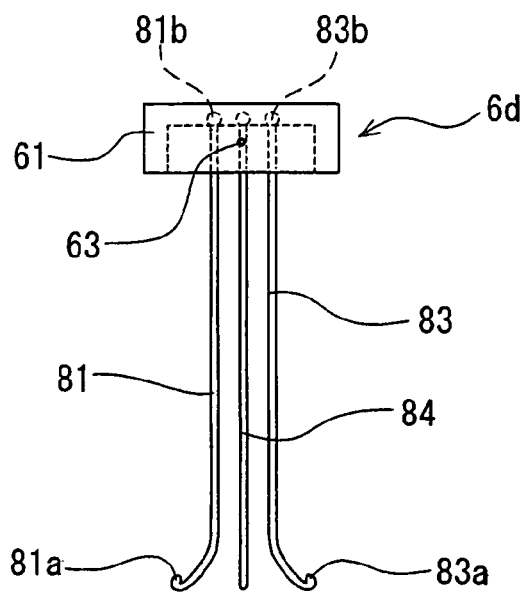
FIG. 18 is a front view of an impeller fixing member used in the blood pump device shown in FIGS. 16 and 17.
Figure 19:
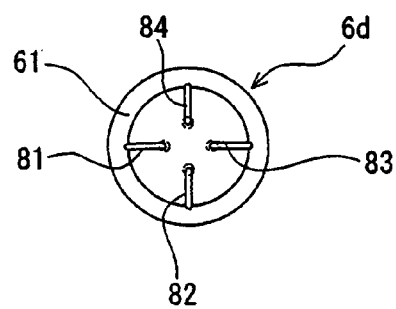
FIG. 19 is a bottom view of the impeller fixing member shown in FIG. 18.

In the impeller fixing member 6*d* in the embodiment shown in FIGS. 18 and 19, the plurality of elongated elastic members are composed of a plurality of (specifically, four) elongated elastic or flexible members 81, 82, 83, 84 which are fixed to the inside surface of the mounting section 61. A tip part of each of the elongated elastic members is bent to the outer side. In addition, the tip-most portions 81*a*, 82*a*, 83*a*, 84*a* of the elongated elastic members are bent end portions which prevent the tip faces of the elastic members from contacting the impeller 5. In addition, the base end portions 81*b*, 82*b*, 83*b*, 84*b* of the elongated elastic members are formed as bulged or enlarged end portions which prevent the elongated elastic members from coming off, or separating from, the mounting section 61.

Figure 17:
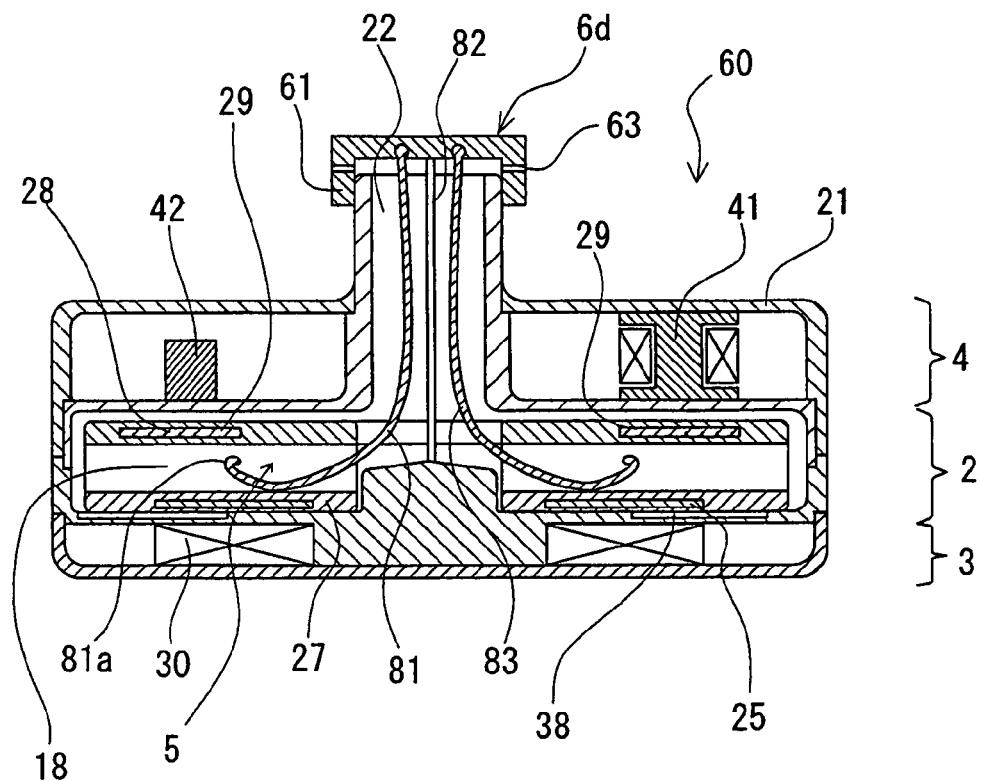
FIG. 17 is a cross-sectional view taken along the section line XVII-XVII of FIG. 16.

In a non-pressed condition illustrated in FIG. 18, the tip portions of the plurality of elongated elastic members enter into the central opening part of the impeller 5. After the tip portions enter into the central opening part of the impeller 5 and come into contact with the inside surface of a housing 21, the elongated elastic members are pushed further, as shown in FIG. 17, whereby the tip portions are curved, bent or flexed, and caused to enter into the impeller 5 through the central opening part of the impeller 5, thereby pressing the disk-shaped lower shroud 27. This ensures that the impeller 5 is pressed against the inside surface of the housing 21 and fixed there.

The deformation mode of the elongated elastic members is not limited to the description above. For example, the elongated elastic members may be so configured that in the non-pressed condition (FIG. 18), their tip portions enter into the central opening part of the impeller 5 and, after their tip portions enter into the central opening part of the impeller 5 and come into contact with the inside surface of the housing 21, they are pushed further so that their end portions are curved and make contact with the disk-shaped lower shroud 27 while the tips thereof contact the inside surface of the upper shroud 28. In this case, the impeller fixing member does not press the impeller 5 against the inside surface of the housing 21, but instead the impeller fixing member itself holds the impeller 5.

In addition, the impeller fixing member 6*d* in this embodiment is mounted to a blood inflow port 22 in a substantially gas-tight condition, and has sterilizing gas passages 63 permitting a sterilizing gas to enter into the inside of the housing 21. The sterilizing gas passages 63 are the same as described above. Also, the sterilizing gas passages 63 may be formed by use of a structure in which the mounting section 61 of the impeller fixing member 6*d* is mounted to the blood inflow port 22 in a non-gas-tight condition. For example, as mentioned above, the sterilizing gas passages may be formed by providing the inside surface of the mounting section 61 of the impeller fixing member 6*d* with ribs.

The material forming the elastic members (elongated elastic members 81, 82, 83, 84) may be any material that has some degree of springiness. Examples of materials which can be used to form the elastic members include metallic materials such as spring high-tensile stainless steel, superelastic alloys, etc., and semi-hard resins such as polyolefins, hard polyurethane, polyacetal, polyimides, fluororesin, hard polyvinyl chloride resin, etc. Incidentally, where the elastic members are formed from a metal, they are preferably coated with a synthetic resin.

In all the impeller fixing members as above-mentioned, the material forming the mounting section 61 may be any material that has some degrees of flexibility and shape-retaining property. Examples of the material which can be used to form the mounting section 61 include polyolefins (polyethylene, polypropylene, ethylene-propylene copolymer), styrene-based resins [polystyrene, MS resin (methacryalte-styrene copolymer), MBS resin (methacrylate-butylene-styrene copolymer)], polyamides (6 nylon, 66 nylon), olefin-based elastomers (polyethylene elastomer, polypropylene elastomer), amide-based elastomers (polyamide elastomer), styrene-based elastomers (e.g., styrne-butadiene-styrene copolymer, styrene-isoprene-styrene copolymer, styrene-ethylenebutylene-styrene copolymer), polyurethane, urethane-based elastomers, synthetic rubbers such as urethane rubber, silicone rubber, butadiene rubber, etc., natural rubbers such as latex rubber, etc., and soft polyvinyl chloride.

In addition, each of the impeller fixing members 6, 6a, 6b, 6c, 6d may be of such a type that it can be mounted to the blood outflow port and it presses the impeller against the inside surface of the housing to fix the impeller through direct contact of the tip portion(s) of the impeller fixing member with the impeller.

Figure 20:
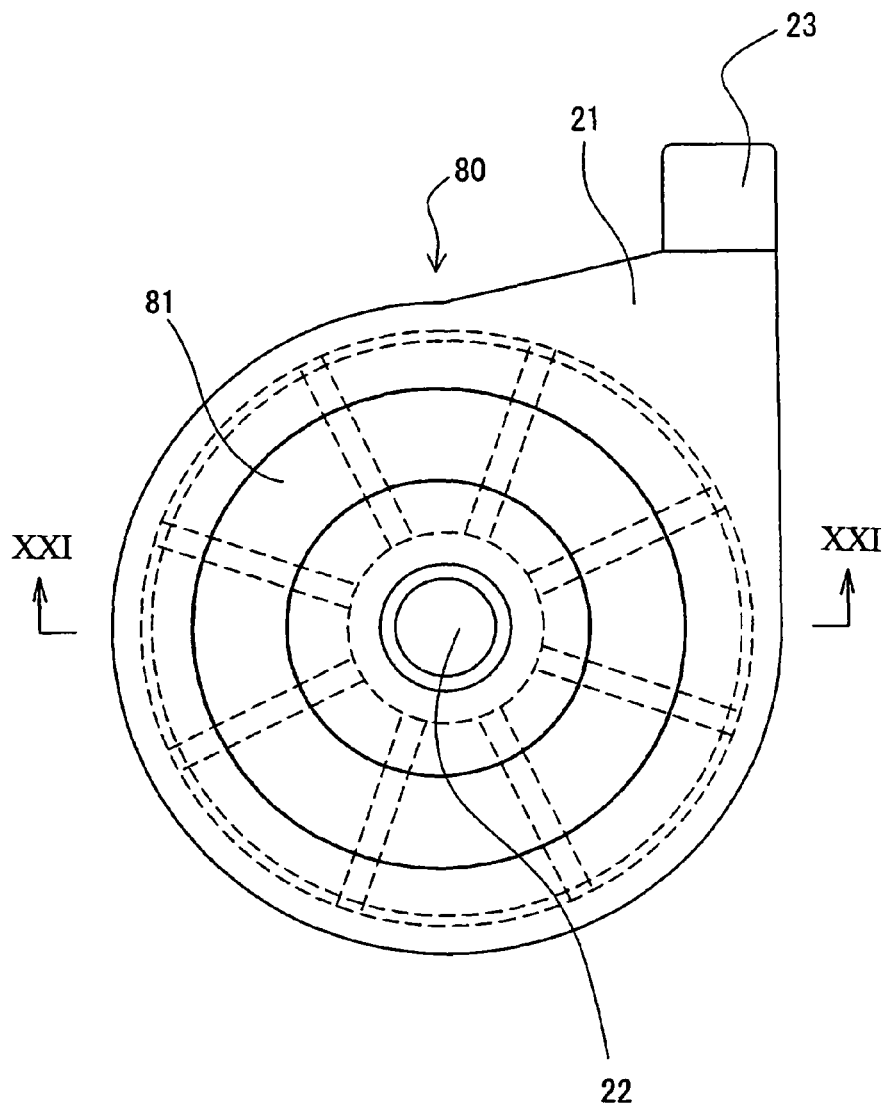
FIG. 20 is a plan view of another embodiment of the blood pump device according to the present invention.
Figure 21:
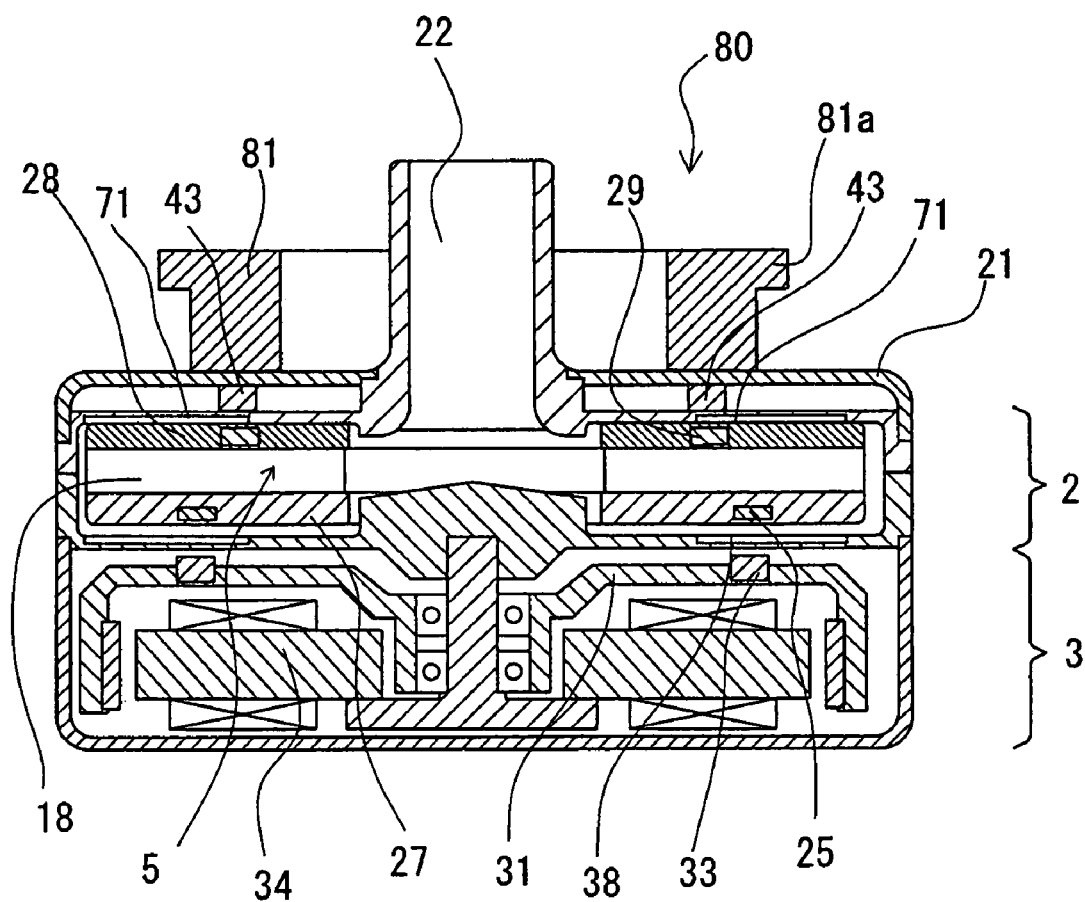
FIG. 21 is a cross-sectional view taken along line XXI-XXI of FIG. 20.

A further alternative construction of the impeller fixing member is shown in FIGS. 20 and 21. As shown in FIG. 21, a blood pump device 80 for which the impeller fixing member 81 in this embodiment is used is of a type similar to that shown in FIGS. 8 and 9. The blood pump device 80 in this embodiment differs from the embodiment shown in FIG. 1 in that it does not include an impeller position control section including electromagnets 41 and position sensors 42. In addition, the blood pump device 80 has a non-contact type bearing mechanism that includes hydrodynamic grooves 38 formed in the inside surface 21a, on the motor 30 side, forming the inside surface of a housing containing the impeller 5 and forming a blood chamber as generally shown in FIG. 6. Further, the blood pump device comprises an impeller rotating torque generating section 3 which is a motor of the type that includes a rotor having permanent magnets, and also an auxiliary impeller attracting permanent magnet.

The impeller 5 in this embodiment also has a plurality of (e.g., five to 40) magnetic bodies 25 (permanent magnets or magnets for coupling) embedded therein. In this embodiment, the magnetic bodies 25 are embedded in a lower shroud 27. The magnetic bodies 25 embedded in the impeller 5 are attracted to the side opposite to a blood inflow port 22 by permanent magnets 33 provided in a rotor 31 of the impeller rotating torque generating section 3 so that a rotating torque generated by the impeller rotating torque generating section 3 is transmitted to the impeller 5.

In addition, with a certain number of the magnetic bodies 25 embedded as in this embodiment, magnetic coupling with the rotor 31 described later can be secured sufficiently. The shape of the magnetic bodies 25 (permanent magnets) is preferably a circle.

As shown in FIG. 21, the impeller rotating torque generating section 3 includes the rotor 31 and a motor 34 for rotating the rotor 31. The rotor 31 includes a plurality of permanent magnets 33 provided in its surface on the blood pump section 2 side. The center of the rotor 31 is fixed to a rotating shaft of the motor 34. The permanent magnets 33 are provided in plural and at regular or equal angular intervals so as to correspond to the layout conditions (the number and positions) of the permanent magnets 25 of the impeller 5.

As mentioned, the blood pump device 80 has the non-contact type bearing mechanism comprised of the hydrodynamic grooves 38 formed in the housing inside surface 21a. The impeller 5 is rotated in a non-contact state by a hydrodynamic bearing effect produced between the impeller 5 and the hydrodynamic grooves 38 through rotation at a rotating speed of not less than a predetermined value.

Further, as shown in FIG. 21, in the blood pump device 80 in this embodiment, the impeller 5 includes a second magnetic member 29 embedded in an upper shroud 28 and provided separately from the magnetic bodies 25, and a fixed permanent magnet 43 for attracting the second magnetic member 29 in the direction opposite to the motor 34. The permanent magnet(s) 43 may be an annular magnet(s) or a plurality of arcuate magnets. The impeller 5 is attracted in opposite directions by both the permanent magnets 33 of the rotor 31 and the permanent magnet(s) 43. The plurality of permanent magnets are arranged at regular or equal angular intervals about the center of the impeller 5. The number of permanent magnet(s) 43 is one or more, and may be, for example, two to six.

Furthermore, the blood pump device 80 in this embodiment preferably includes second hydrodynamic grooves 71 formed in the inside surface of the housing 21, on the side of the housing adjacent the permanent magnet 43 or in a surface of the impeller facing towards the permanent magnet 43 (i.e., on the permanent magnet 43 side of the impeller 5).

In this version of the blood pump device 80, the impeller 5 is in the state of being attracted in opposite directions, i.e., toward the motor side and toward the blood inflow port side, and insofar as there is no considerable difference between the two attracting forces, the position of the impeller 5 would be instable, and the impeller 5 may quite possibly move inside the housing 21.

As shown in FIG. 20, the impeller fixing member 81 is detachably mounted to the housing by the permanent magnet(s) 43, and includes an annular magnetic body or annular permanent magnet or a plurality of magnetic bodies or permanent magnets arranged in an annular pattern for attracting the impeller 5 on the housing inside surface in the direction opposite to the impeller rotating torque generating section 3 to thereby fix the impeller 5.

The impeller fixing member 81 in this embodiment can be detachably mounted to the housing, and includes an annular permanent magnet for attracting the magnetic members 29 of the impeller 5 in the direction opposite to the impeller rotating torque generating section 3. The impeller fixing member 81 may include a plurality of permanent magnets arranged in an annular pattern rather than an annular permanent magnet. Further, instead of the permanent magnet(s), the impeller fixing member 81 may include an annular magnetic body or a plurality of magnetic bodies arranged in an annular pattern.

The impeller fixing member 81 is a member for amplifying the magnetic force(s) of the auxiliary attracting permanent magnet(s) 43 of the pump device 80 or a member for directly attracting the second magnetic members 29 of the impeller 5. Therefore, the impeller 5 is strongly attracted in the direction opposite to the impeller rotating torque generating section 3, and is brought into close contact with the housing inside surface, so as to be fixed. The permanent magnet(s) of the impeller fixing member 81 is so arranged as to corresponding to the layout conditions of the auxiliary attracting permanent magnet(s) 43 or the second magnetic member(s) 29 of the impeller 5. In addition, the impeller fixing member 81 is provided with an annular flange part 81a for use at the time of dismounting. The impeller fixing member may be split into a plurality of pieces, for example the impeller fixing member can preferably be split into two semi-circular halves.

This type of blood pump device is so designed that no large difference is generated between the attractive force acting between the magnetic member(s) 29 of the impeller 5 and the auxiliary attracting permanent magnet(s) 43, and the attractive force acting between the magnetic bodies 25 of the impeller 5 and the permanent magnets 33 of the rotor. As a result, the impeller 5 may be attracted, during non-operation (non-levitating time), to the housing inside surface on the auxiliary attracting permanent magnet side or to the housing inside surface on the rotor side. If the impeller fixing member 81 is mounted in a situation where the impeller 5 is attracted onto the rotor side, the impeller 5 is attracted to the housing inside surface on the auxiliary attracting permanent magnet side upon the occurrence of an impact. To avoid this, the attractive force acting between the magnetic member(s) 29 of the impeller 5 and the auxiliary attracting permanent magnet(s)

43 is designed to be slightly greater than the attractive force acting between the magnetic bodies 25 of the impeller 5 and the permanent magnets 33.

In addition, the force F for fixing the impeller by the impeller fixing member may generally be set as follows. Movements of the impeller associated with vibrations or an impact load during storage and transportation can be securely suppressed if the following condition is satisfied:

$$F > ma,$$

where F is the force for fixing the impeller, m is the mass of the impeller, and a is an expected acceleration of disturbance.

Figure 22:
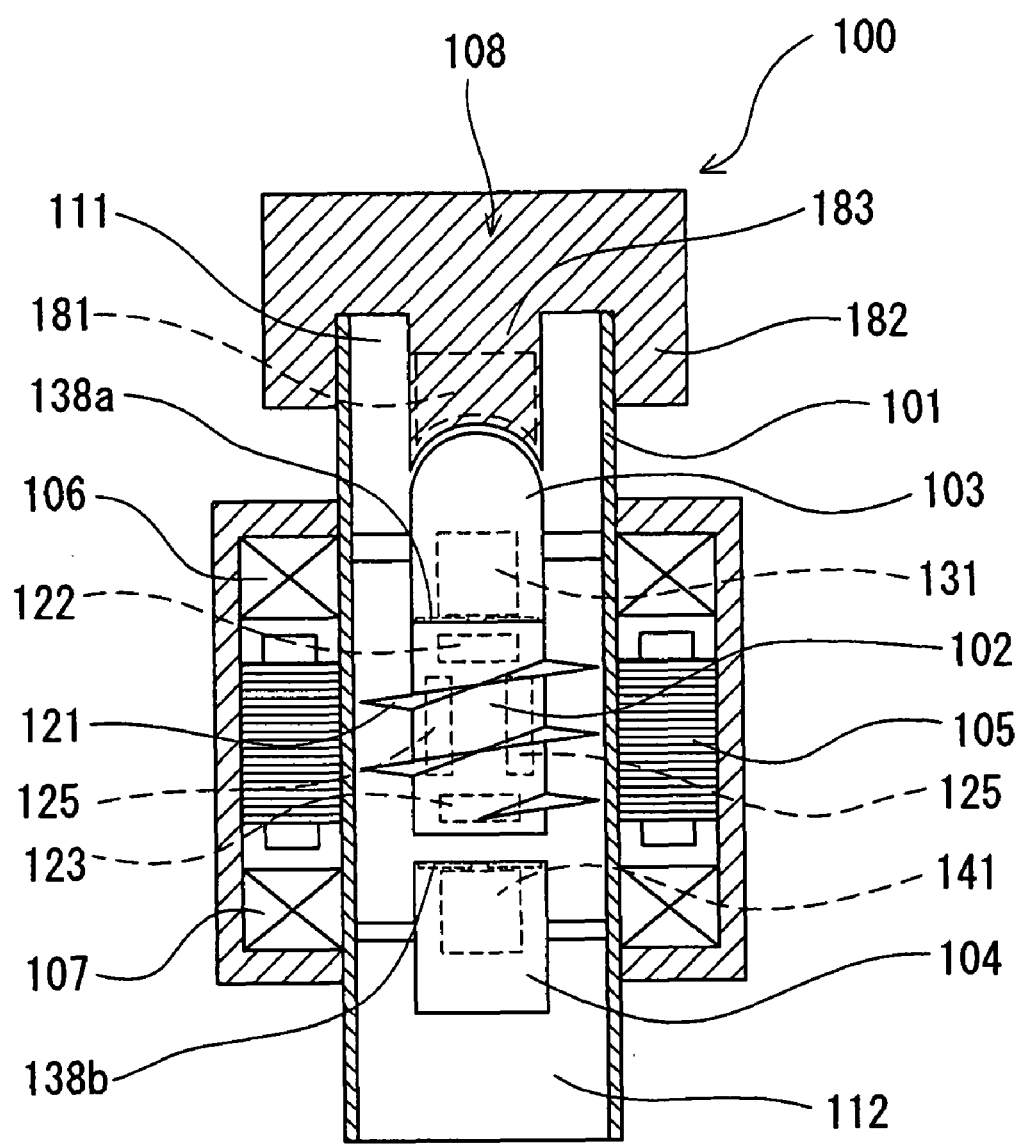
FIG. 22 is a cross-sectional view of a further embodiment of the blood pump device disclosed herein.

Another embodiment of a blood pump device 100 is illustrated in FIG. 22. In the blood pump device 100 of this embodiment, the pump device includes: a housing 101 having a blood inflow port 111 and a blood outflow port 112, an impeller 102 including magnetic bodies 125 and rotated inside the housing 101 in a non-contact state in relation to the inside surface of the impeller 101 so as to feed blood; an impeller rotating torque generating section 105 for rotating the impeller 102 by acting on the impeller 102 from the outside of the housing 101; and a non-contact type bearing mechanism 106, 107 for enabling rotation in the non-contact state of the impeller 102 inside the housing 101. In addition, the blood pump device 100 includes an impeller fixing member 108 which is detachably mounted to the housing 101 and prevents the impeller 102 from moving inside the housing 101.

While all the blood pump devices in the above-described embodiments are centrifugal type blood pump devices, the blood pump device 100 in this embodiment is an axial flow type blood pump device and is a magnetic bearing type axial flow type blood pump device.

In this blood pump device 100, the housing 101 is hollow cylindrical in shape as shown in FIG. 22, has a blood inflow port 111 on the upper end side and a blood outflow port 112 on the lower end side.

A solid cylindrical impeller 102 is contained in the housing 101. The impeller 102 has a blood transfer fin 121 provided on a side surface thereof, and is provided therein with the side surface side magnetic bodies 125 to which a rotating force is imparted from the impeller rotating torque generating section, an upstream-side magnetic body 122 provided in the inside of and on the upper end side of the impeller 102, and a downstream-side magnetic body 123 provided in the inside of and on the lower end side of the impeller 102. The side surface side magnetic bodies 125, the upstream-side magnetic body 122 and the downstream-side magnetic body 123 are each composed of a magnetic material or a permanent magnet. Particularly, they are each preferably composed of a permanent magnet.

In addition, the housing 101 has an upstream-side impeller attracting section 103 which is disposed in the vicinity of and on the upstream side of the impeller 102 and which is provided therein with a magnetic member 131. Specifically, the upstream-side impeller attracting section 103 is a part referred to as a flow straightener, and its upper end is formed in a roughly hemispherical shape as shown in the figure so as to enable relatively good dispersion of blood. The magnetic member 131 provided in the upstream-side impeller attracting section 103 and the upstream-side magnetic body 122 provided in the impeller 102 are capable of magnetic attraction. The housing 101 also has a downstream-side impeller attracting section 104 provided therein with a magnetic member 141. Specifically, the downstream-side impeller attracting section 104 is a part referred to as a diffuser. The magnetic member 141 provided in the downstream-side impeller attracting section 104 and the downstream-side magnetic body 123 provided in the impeller 102 are capable of magnetic attraction. Therefore, the impeller 102 is attracted in both the upper end and lower end directions (upstream and downstream). The magnetic member 131 provided in the upstream-side impeller attracting section 103 and the magnetic body 141 provided in the downstream-side impeller attracting section 104 are each composed of a magnetic material or a permanent magnet.

In the blood pump device 100 in this embodiment, the impeller rotating torque generating section includes a stator coil type motor 105 having a plurality of stator coils surrounding the side surface of the impeller 102 to attract the magnetic bodies 125 of the impeller 102 and rotate the impeller 102 when being electrically energized.

Further, in the blood pump device 100 in this embodiment, a non-contact type bearing mechanism includes a magnetic force regulating means which includes a first electromagnet 106 for imparting a magnetic force to, or amplifying a magnetic force of, the magnetic member 131 of the upstream-side impeller attracting section 103 when electrically energized, and a second electromagnet 107 for imparting a magnetic force to, or amplifying a magnetic force of, the magnetic body 141 of the downstream-side impeller attracting section 104 electrically energized. More accurately, the non-contact type bearing mechanism includes the two electromagnets 106, 107, the upstream-side magnetic body 122 and the downstream-side magnetic body 123 of the impeller 102, the magnetic member 131 of the upstream-side impeller attracting section 103, and the magnetic member 141 of the downstream-side impeller attracting section 104. By regulating the current supplied to the two electromagnets 106, 107, the impeller 102 is rotated without making contact with the housing inside surface inclusive of the upstream-side impeller attracting section 103 and the downstream-side impeller attracting section 104.

In addition, in the blood pump device 100 in this embodiment, as shown in FIG. 22, the upstream-side impeller attracting section 103 has first hydrodynamic grooves 138a (hydrodynamic pressure generating means) and/or the downstream-side impeller attracting section 104 has second hydrodynamic grooves 138b (hydrodynamic pressure generating means). The first hydrodynamic grooves are provided in the upstream-side impeller attracting section inside surface for generating hydrodynamic pressure. The second hydrodynamic grooves are provided in the downstream-side impeller attracting section inside surface for generating hydrodynamic pressure.

The impeller 102 can be rotated in a non-contact state by a hydrodynamic bearing effect produced between the impeller 102 and the hydrodynamic grooves 138a and/or 138b due to rotation at a rotating speed of not less than a predetermined value in the condition where the operation of the electromagnets 106 is stopped. In the blood pump device of the type in this embodiment, the hydrodynamic grooves need not necessarily be provided.

An impeller fixing member 108 in this embodiment includes a detachable mounting section 182 for mounting to a blood inflow port 111 of the housing 101, and an entering section 183 extending from the mounting section 182 and entering into (positioned in) the port. The entering section 183 has a permanent magnet 181 for imparting a magnetic force to, or amplifying a magnetic force of, the magnetic member 131 of the upstream-side impeller attracting section 103. Specifically, the entering section 183 is a projecting part having an outer diameter smaller than the inner diameter of the blood inflow port 111, and its tip portion is a roughly hemispherical recessed portion corresponding to the roughly hemispherical shape of the tip part of the upstream-side impeller attracting section 103. In addition, the permanent magnet 181 is embedded in the tip portion of the entering section 183. The permanent magnet 181 may have an exposed surface.

In the blood pump device 100 in this embodiment, with the impeller fixing member 108 mounted, the impeller 102 is strongly attracted toward the upstream-side impeller attracting section 103 side, and its upper end face is brought into close contact with the lower end face of the upstream-side impeller attracting section 103 and is thereby fixed.

As shown in FIG. 22, the mounting section 182 of the impeller fixing member 108 is preferably fitted to the outside surface (or inside surface) of the blood inflow port 111 of the housing 101. The impeller fixing member 108 may be provided with a fixing and retaining mechanism (e.g., screw thread) for fixing it to and retaining it on the blood pump device 100. Further, in the case where the attractive force acting between the permanent magnet 181 of the impeller fixing member 108 and the magnetic member 131 of the upstream-side impeller attracting section 103 ensures that the impeller fixing member 108 will not easily come off from the housing 101, a mounting means for retaining a fixed state may not necessarily be provided. In the case where the impeller fixing member 108 in this embodiment is mounted to the blood inflow port 111 in a substantially gas-tight condition, like the above-described impeller fixing member 6, sterilizing gas passages (not shown) permitting a sterilizing gas to enter into the inside of the housing may be provided. The sterilizing gas passages are the same described above.

Figure 23:
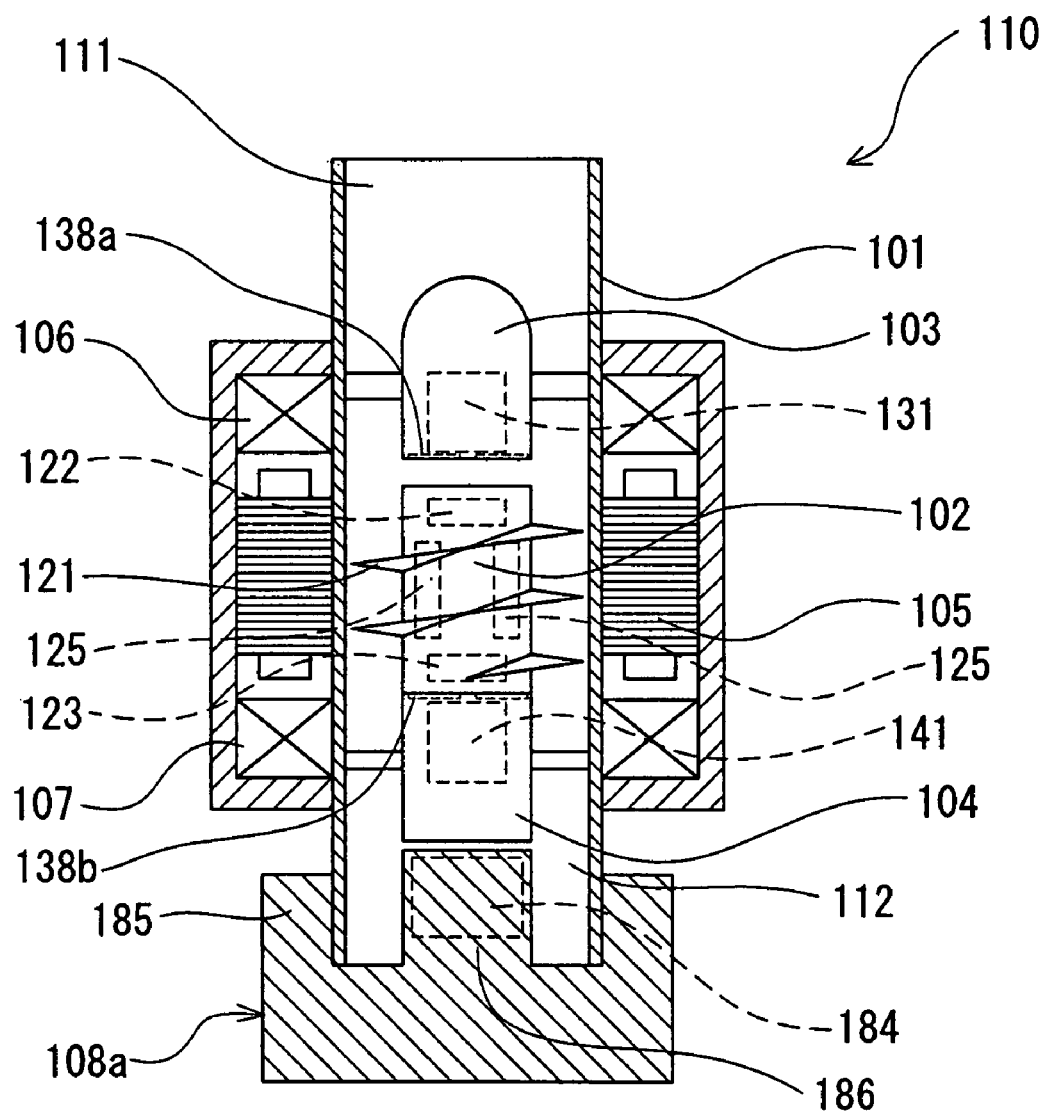
FIG. 23 is a cross-sectional view of yet another embodiment of the blood pump device disclosed herein.

In addition, the impeller fixing member may be of the type as shown in FIG. 23. The impeller fixing member 108a in the blood pump device 110 in this embodiment is the same as the above-described impeller fixing member 108 in its basic configuration. The difference between the two lies in that the impeller fixing member 108 of the FIG. 22 embodiment is mounted to the blood inflow port 111 side of the housing 101, whereas the impeller fixing member 108a of the FIG. 23 embodiment is mounted to the blood outflow port 112 side of a housing 101.

The impeller fixing member 108a includes a detachable mounting section 185 for mounting to the blood outflow port 112 of the housing 101, and an entering section 186 extending from the mounting section 185 and entering into (positioned in) the port 112. The entering section 186 includes a permanent magnet 184 for imparting a magnetic force to, or amplifying a magnetic force of, a magnetic member 141 of a downstream-side impeller attracting section 104.

Specifically, the entering section 186 is a projecting part having an outer diameter smaller than the inner diameter of the blood outflow port 112, and its tip portion has a shape corresponding to the shape of an end part of the downstream-side impeller attracting section 104. The permanent magnet 184 is embedded in the tip portion of the entering section 186. The permanent magnet 184 may have an exposed surface.

In the blood pump device 110 in this embodiment, with the impeller fixing member 108a mounted, whereby the impeller 102 is strongly attracted toward the downstream-side impeller attracting section 104 side, and its lower end face is brought into close contact with the upper end face of the downstream-side impeller attracting section 104 and is thereby fixed. In addition, as shown in FIG. 23, the mounting section 185 of the impeller fixing member 108a is preferably fitted to the outside surface (or inside surface) of the blood outflow port 112 of the housing 101. The impeller fixing member 108a may be provided with a fixing and retaining member (e.g., screw thread) for fixing the impeller fixing member to, and retaining it on, the housing 101. Further, in a situation where the attractive force acting between the permanent magnet 184 of the impeller fixing member 108a and the magnetic member 141 of the impeller attracting section 104 ensures that the impeller fixing member 108a would not easily come off from the housing 101, a mounting means for retaining a fixed state may not need to be provided. In the situation where the impeller fixing member 108a in this embodiment is mounted to the blood outflow port 112 in a substantially gas-tight condition, like the above-described impeller fixing member 6, sterilizing gas passages permitting a sterilizing gas to enter into the inside of the housing 101 may be provided. The sterilizing gas passages are the same as described above.

Figure 24:
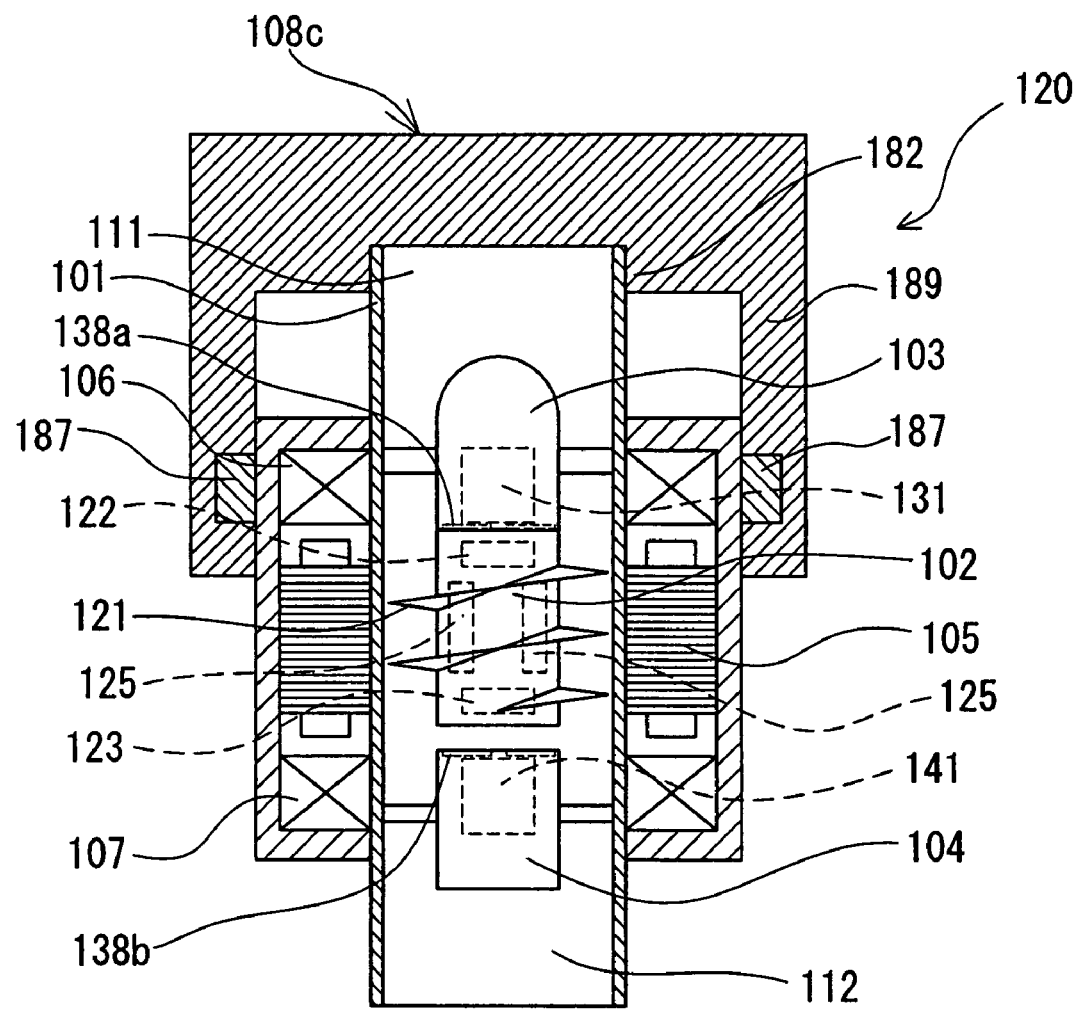
FIG. 24 is a cross-sectional view of a yet further embodiment of the blood pump device disclosed herein.

The impeller fixing member may alternatively be of the type shown in FIG. 24. The difference between the blood pump device 120 in this embodiment and the above-described blood pump device 100 resides in the impeller fixing member.

The impeller fixing member 108c in this embodiment includes a detachable mounting section 182 for mounting to a blood inflow port 111 or a blood outflow port 112 of a housing 101, and an extension section 189 extending from the mounting section 182 in the direction of the impeller 102 through the outside of the housing 101. The extension section 189 has permanent magnets 187 for directly or indirectly attracting a magnetic body of the impeller 102. The impeller fixing member 108c in the embodiment shown in FIG. 24 includes the detachable mounting section 182 for mounting to the blood inflow port 111 of the housing 101, and the extension section 189 extending from the mounting section 182 in the direction of the impeller 102 through the outside of the housing 101. The extension section 189 has the permanent magnets 187 for attracting the magnetic body 122 of the impeller 102. The permanent magnets 187 are preferably provided as a plurality of permanent magnets in a tip portion of the extension section 189. In addition, the plurality of permanent magnets are preferably arranged so as to be at equal angles with respect to the center axis of the housing 101 when mounted to the housing 101.

The impeller fixing member 108c attracts the magnetic body 122 of the impeller 102, and imparts a magnetic force to, or amplifies a magnetic force of, the magnetic member 131 of the upstream-side impeller attracting section 103. In the blood pump device 120 in this embodiment, the impeller fixing member 108c is mounted and configured such that the impeller 102 is attracted toward the upstream-side impeller attracting section 103 side, and its upper end face is brought into close contact with the lower end face of the upstream-side impeller attracting section 103 and is thereby fixed.

As shown in FIG. 24, the mounting section 182 of the impeller fixing member 108c is preferably fitted to the outside surface (or inside surface) of a blood inflow port 111 of the housing 101. In addition, the impeller fixing member 108c may be provided with a fixing and retaining member (e.g., screw thread) for fixing it to and retaining it on the housing 101. Further, in situations where the attractive forces acting between the permanent magnet 187 of the impeller fixing member 108c and the impeller attracting section 103 and the impeller 102 ensure that the impeller fixing member 108c will not easily come off from the housing 101, a mounting means for retaining a fixed state may not need to be provided.

When the impeller fixing member 108c in this embodiment is mounted to the blood inflow port 111 in a substantially gas-tight condition, like the above-described impeller fixing member 6, sterilizing gas passages permitting a sterilizing gas to enter into the inside of the housing 101 may be provided. The sterilizing gas passages can be similar to those described above.

While the impeller fixing member 108c in this embodiment is mounted to the blood inflow port 111 side of the housing 101, other variations are possible. For example, this type of impeller fixing member 108c may be mounted to the blood outflow port 112. In that case, the impeller fixing member would include a detachable mounting section for mounting to the blood outflow port 112, an extension section 189 extending from the mounting section in the direction of the impeller 102 through the outside of the housing 101, and a permanent magnet provided in the extension section 189 for the purpose of attracting a magnetic body of the impeller 102.

Figure 25:
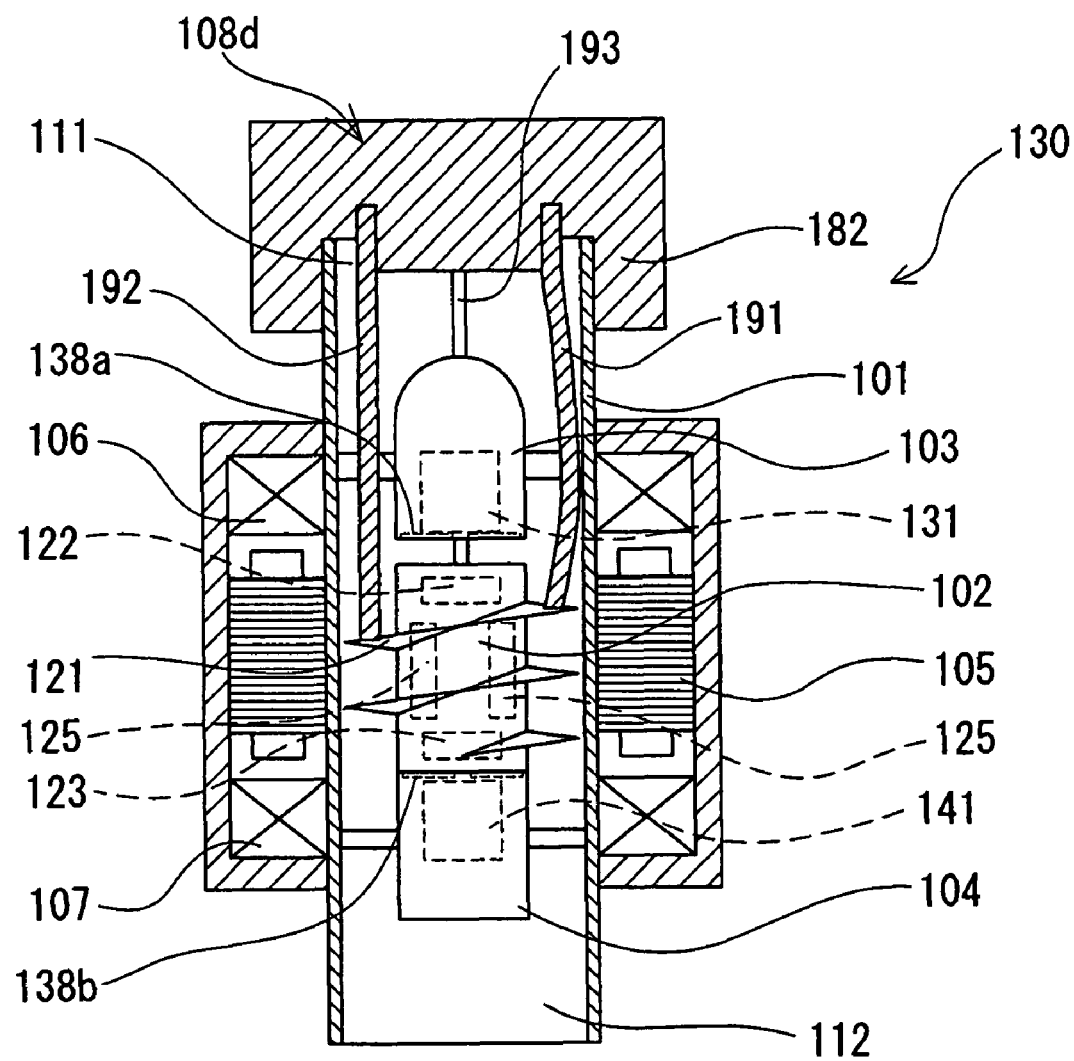
FIG. 25 is a cross-sectional view of still another embodiment of the blood pump device.

The impeller fixing member may also be of the type shown in FIG. 25. The difference between the blood pump device 130 of this embodiment and the above-described blood pump device 100 resides in the impeller fixing member.

The impeller fixing member 108d in this embodiment includes a detachable mounting section 182 for mounting to a blood inflow port 111 or a blood outflow port 112 of a housing 101, and an entering section extending from the mounting section 182 and entering into the port. The entering section includes impeller pushing parts 191, 192, 193 adapted to push the impeller 102.

More specifically, the impeller fixing member 108d includes the detachable mounting section 182 for mounting to the blood inflow port 111 or the blood outflow port 112 of the housing 101, and the elastic impeller pushing parts 191, 192, 193 positioned in the port and adapted to push the fins 121 of the impeller 102. The elastic impeller pushing parts 191, 192, 193 are formed in a rod-like shape, with a plurality of the pushing parts being provided. One end of each of the elastic impeller pushing parts 191, 192, 193 is fixed to the inside surface part at the peripheral edge part of the impeller fixing member 108d, and the opposite end is a free end for pushing the fin 121 of the impeller 102.

In the blood pump device 130 in this embodiment, the impeller fixing member 108d is mounted, whereby the impeller 102 is pushed toward the downstream-side in the direction of the impeller attracting section 104 so that the lower end face of the impeller 102 is brought into close contact with the upper end face of the downstream-side impeller attracting section 104 and is thereby fixed. As shown in FIG. 25, the mounting section 182 of the impeller fixing member 108d is preferably fitted to the outside surface (or inside surface) of the blood inflow port 111 of the housing 101. In addition, the impeller fixing member 108d may be provided with a fixing and retaining member (e.g., screw thread) for fixing the impeller fixing member 108d to and retaining it on the housing 101. In the case where the impeller fixing member 108d in this embodiment is mounted to the blood inflow port 111 in a substantially gas-tight condition, like the above-described impeller fixing member 6, sterilizing gas passages can be provided to permit a sterilizing gas to enter into the inside of the housing 101. The sterilizing gas passages can be the same as those described above.

While the impeller fixing member 108d in this embodiment is mounted to the blood inflow port 111 side of the housing 101, other alternatives are possible. This type of impeller fixing member 108d may be mounted to a blood outflow port 112. In that case, the impeller fixing member would include a detachable mounting section for mounting to the blood outflow port 112, an entering section extending from the mounting section and entering into or positioned in the port, and the entering section includes impeller pushing parts 191, 192, 193 capable of pushing the impeller 102.

The material forming the elastic impeller pushing parts may be any material that has some degree of elasticity. Examples of the material which can be used to form the elastic impeller pushing parts include olefin-based elastomers (polyethylene elastomer, polypropylene elastomer), amide-based elastomer (polyamide elastomer), styrene-based elastomer (e.g., styrene-butadiene-styrene copolymer, styrene-isoprene-styrene copolymer, styrene-ethylenebutylene-styrene copolymer), polyurethane, urethane-based elastomer, synthetic rubbers such as urethane rubber, silicone rubber, butadiene rubber, etc., natural rubbers such as latex rubber, etc., and soft polyvinyl chloride.

In all the embodiments of the axial flow type blood pump device above, a magnetic bearing type axial flow blood pump device is used, but the disclosed blood pump device is not limited in this respect. For example, a hydrodynamic bearing type axial flow blood pump may also be used.

The force F for fixing the impeller by the various embodiments of the impeller fixing member (impeller fixing means) disclosed herein may generally be as follows. Movements of the impeller upon vibrations and impact loads during storage and transportation can be suppressed securely if the following condition is satisfied:

$$F > ma,$$

where F is the force for fixing the impeller, m is the mass of the impeller, and a is an expected acceleration of disturbance.

The principles, preferred embodiments and other disclosed aspects have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A blood pump device comprising:
a housing having a blood inflow port and a blood outflow port;
an impeller rotatably positioned inside the housing to feed blood, the impeller being provided with a magnetic body;
an impeller rotating torque generating section attracting the impeller from outside the housing and rotating the impeller;
a non-contact type bearing mechanism enabling rotation of the impeller in the housing in a non-contact state relative to an inside surface of the housing; and
an impeller fixing member detachably mounted to the housing and preventing the impeller from moving inside the housing;
wherein:
the blood pump device is a centrifugal type blood pump device;
the housing comprises a blood passage extending from the blood inflow port;
the impeller comprises a central opening part located on an extension line of the blood passage;
the impeller fixing member comprises a detachable mounting section detachably mounted to the blood inflow port, and an impeller fixing section extending from the mounting section, the impeller fixing section being positioned in the blood passage and applying a force to the impeller to hold the impeller or press the impeller against the inside surface of the housing to fix the impeller against movement.

2. The blood pump device as set forth in claim 1, wherein the impeller fixing section comprises an impeller pressing part pressing a peripheral edge portion of the central opening part of the impeller.

3. The blood pump device as set forth in claim 2, wherein the impeller fixing section comprises an elastic tip part positioned in the central opening part of the impeller and hold the impeller against movement by elastic deformation.

4. The blood pump device as set forth in claim 3, wherein the elastic tip part is an elastic spherical part, a balloon inflatable by injection of a fluid, or a tubular part having a plurality of slits in its side surface.

5. The blood pump device as set forth in claim 1, wherein the impeller comprises a disk-shaped lower shroud, and the impeller fixing section comprises a plurality of elongated elastic members passing through the central opening part of the impeller and positioned in the impeller to apply a force to the disk-shaped lower shroud fixing the impeller against movement.

6. The blood pump device as set forth in claim 2, wherein:
the blood pump device is a centrifugal type blood pump device;
the housing comprises a blood passage extending from the blood outflow port;
the impeller comprises an upper shroud and a lower shroud between which is positioned a vane; and
the impeller fixing member comprises a detachable mounting section detachably mounted to the blood outflow port, and an impeller fixing section extending from the mounting section and passing through the blood outflow port and into the blood passage, and applying a force to the impeller to either hold the impeller or press the impeller against the inside surface of the housing to fix the impeller against moving.

7. The blood pump device as set forth in claim 1, wherein:
the impeller rotating torque generating section is a stator coil type motor having a plurality of stator coils arranged in a circle to attract the magnetic body of the impeller from one side of the impeller and rotate the impeller upon being electrically energized; and
the non-contact type bearing mechanism comprises a hydrodynamic groove formed on the inside surface of the housing on a side of the housing adjacent the stator coil type motor.

8. The blood pump device as set forth in claim 1, wherein:
the impeller rotating torque generating section is a stator coil type motor having a plurality of stator coils arranged in a circle to attract the magnetic body of the impeller from one side of the impeller and rotate the impeller upon being electrically energized; and
the non-contact type bearing mechanism comprising a magnetic member provided at an upper shroud of the impeller and an electromagnet which attracts the magnetic member of the impeller in a direction opposite to the impeller rotating torque generation section.

9. The blood pump device as set forth in claim 1, wherein:
the impeller rotating torque generating section comprises a rotor having a magnet for attracting the magnetic body of the impeller and a motor for rotating the rotor;
the non-contact type bearing mechanism comprises a hydrodynamic groove formed in the inside surface of the housing on a side of the housing adjacent the motor;
the impeller comprises an upper shroud at which is mounted a magnetic member; and
the blood pump device further comprises a permanent magnet which attracts the magnetic member of the impeller in a direction opposite to the impeller rotating torque generating section.

10. The blood pump device as set forth in claim 9, wherein:
the impeller fixing member is detachably mounted to the housing by the permanent magnet and comprises an annular magnetic body, an annular permanent magnet or a plurality of magnetic bodies or permanent magnets arranged annularly, to fix the impeller by attracting the impeller onto the inside surface of the housing in a direction opposite to the impeller rotating torque generating section.

11. The blood pump device as set forth in claim 2, wherein:
the impeller rotating torque generating section comprises a stator coil type motor in which a plurality of stator coils surround a side surface of the impeller to attract the magnetic body of the impeller and rotate the impeller upon being electrically energized; and the non-contact type bearing mechanism comprises an upstream-side impeller attracting section comprising a magnetic member and disposed in a vicinity of and on an upstream side of the impeller and having a magnetic member therein, a downstream-side impeller attracting section comprising a magnetic member and disposed in the vicinity of and on a downstream side of the impeller, a first electromagnet for imparting a magnetic force to or amplifying a magnetic force of the magnetic member of the upstream-side impeller attracting section upon being electrically energized and a second electromagnet for imparting a magnetic force to or amplifying a magnetic force of the magnetic member of the downstream-side impeller attracting section upon being electrically energized, or hydrodynamic pressure generating means which includes a first hydrodynamic groove formed in a surface, facing the impeller, of the upstream-side impeller attracting section and a second hydrodynamic groove formed in a surface, facing the impeller, of the downstream-side impeller attracting section.

12. The blood pump device as set forth in claim 11, wherein:
the impeller fixing member comprises a mounting section and an entering section extending from the mounting section, the mounting section being either detachably mounted to the blood inflow port while the entering section extends into the blood inflow port or detachably mounted to the blood outflow port while the entering section extends into the blood outflow port;
the entering section comprises a permanent magnet for imparting a magnetic force to or amplifying a magnetic force of the magnetic member of the upstream-side impeller attracting section or the downstream-side impeller attracting section.

13. The blood pump device as set forth in claim 11, wherein:
the impeller fixing member comprises a mounting section and an extension section extending from the mounting section, the mounting section being either detachably mounted to the blood inflow port while the extension section extends towards the impeller or detachably mounted to the blood outflow port while the extension section extends towards the impeller;
and the extension section comprises a permanent magnet for attracting the magnetic body of the impeller.

14. The blood pump device as set forth in claim 11, wherein:

the impeller fixing member comprises a mounting section and an entering section extending from the mounting section, the mounting section being either detachably mounted to the blood inflow port while the entering section extends into the blood inflow port or detachably mounted to the blood outflow port while the entering section extends into the blood outflow port; and the entering section comprises an impeller pushing part applying a force to the impeller to fix the impeller against movement.

15. The blood pump device as set forth in claim 1, wherein the impeller fixing member comprises a gas passage permitting a sterilizing gas to enter into the housing.

16. A blood pump device comprising:

a housing having a blood inflow port and a blood outflow port;

an impeller rotatably positioned inside the housing to feed blood, the impeller being provided with a magnetic body;

a motor positioned outside the housing and operable to rotate the impeller;

a non-contact type bearing mechanism enabling rotation of the impeller in the housing in a non-contact state relative to an inside surface of the housing;

a mounting section detachably mounted on the housing; and an entering section extending from the mounting section, the entering section passing through the blood inflow port into the housing and engaging the impeller to fix the impeller against movement.

17. The blood pump device as set forth in claim 16, wherein the motor is a stator coil type motor.

18. The blood pump device as set forth in claim 16, further comprising a rotor fixed to a shaft of the motor and provided with a plurality of magnets.

* * * * *